United States Patent
Oglaza et al.

(10) Patent No.: US 11,986,396 B2
(45) Date of Patent: May 21, 2024

(54) IMPLANT FOR RESTORING HEIGHT OF A VERTEBRAL BODY

(71) Applicant: Stryker European Operations Limited, Carrigtwohill (IE)

(72) Inventors: Jean-Francois Oglaza, Portage, MI (US); Eleftherios Louvis, Carringaline (IE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 18/088,861

(22) Filed: Dec. 27, 2022

(65) Prior Publication Data

US 2023/0130342 A1  Apr. 27, 2023

Related U.S. Application Data

(63) Continuation of application No. 16/722,939, filed on Dec. 20, 2019, now Pat. No. 11,540,926.

(30) Foreign Application Priority Data

Nov. 1, 2019  (GR) ............................... 20190100491

(51) Int. Cl.
*A61F 2/44* (2006.01)
*B33Y 30/00* (2015.01)

(52) U.S. Cl.
CPC ............. *A61F 2/4465* (2013.01); *B33Y 30/00* (2014.12)

(58) Field of Classification Search
None
See application file for complete search history.

(56) References Cited

U.S. PATENT DOCUMENTS

| 5,059,193 | A  | 10/1991 | Kuslich |
| 6,224,604 | B1 | 5/2001  | Suddaby |
| 7,507,241 | B2 | 3/2009  | Levy et al. |
| 7,846,206 | B2 | 12/2010 | Oglaza et al. |

(Continued)

FOREIGN PATENT DOCUMENTS

WO  2008044057 A1  4/2008

OTHER PUBLICATIONS

International Search Report for Application No. PCT/IB2021/050643 dated Oct. 25, 2021, 2 pages.

*Primary Examiner* — Tessa M Matthews
(74) *Attorney, Agent, or Firm* — Howard & Howard Attorneys PLLC

(57) ABSTRACT

An implant for restoring height of a vertebral body. The implant includes upper and lower plates configured to be moved away from one another in the craniocaudal direction. A first support and a second support are arranged to crisscross in a proximal-to-distal direction to facilitate increased expansion of the implant, and a third support and a fourth support may be arranged to crisscross in the proximal-to-distal direction. Certain supports may be laterally spaced from one another to define a void space for receiving a retaining element. An upper support fork may include a first pair of supports arranged in a V-shaped configuration and converge at an apex that is coupled to an underside of the upper plate. A lower support fork may include a second pair of supports arranged in a V-shaped configuration and converge at another apex that is coupled to an upper side of the lower plate.

19 Claims, 22 Drawing Sheets

(56) References Cited

U.S. PATENT DOCUMENTS

| | | |
|---|---|---|
| 8,986,386 B2 | 3/2015 | Oglaza et al. |
| 9,408,707 B2 | 8/2016 | Oglaza et al. |
| 9,414,933 B2 | 8/2016 | Banouskou |
| 9,579,130 B2 | 2/2017 | Oglaza et al. |
| 10,098,751 B2 | 10/2018 | Oglaza et al. |
| 11,540,926 B2 | 1/2023 | Oglaza et al. |
| 2005/0070911 A1 | 3/2005 | Carrison et al. |
| 2005/0228391 A1 | 10/2005 | Levy et al. |
| 2007/0173826 A1 | 7/2007 | Canaveral et al. |
| 2008/0114367 A1* | 5/2008 | Meyer .................... A61F 2/442 606/191 |
| 2008/0183204 A1 | 7/2008 | Greenhalgh et al. |
| 2009/0281628 A1 | 11/2009 | Oglaza et al. |
| 2014/0135780 A1 | 5/2014 | Lee et al. |
| 2015/0282797 A1 | 10/2015 | O'Neil et al. |
| 2016/0242927 A1 | 8/2016 | Seifert et al. |
| 2016/0317188 A1 | 11/2016 | Oglaza et al. |
| 2017/0165790 A1 | 6/2017 | McCarthy et al. |
| 2017/0309282 A1* | 10/2017 | Mani .................... G10L 19/012 |
| 2018/0296361 A1* | 10/2018 | Butler .................. A61F 2/4455 |
| 2018/0353642 A1 | 12/2018 | Lee et al. |
| 2019/0008653 A1 | 1/2019 | Oglaza et al. |

* cited by examiner

IMPLANT FOR RESTORING HEIGHT OF A VERTEBRAL BODY

CROSS-REFERENCE TO RELATED APPLICATIONS

This is a continuation of copending U.S. application Ser. No. 16/722,939, filed Dec. 20, 2019, which claims priority to and all the benefits of Greek Application No. 20190100491, filed Nov. 1, 2019, the entire contents of each being hereby incorporated by reference.

BACKGROUND

A common source of back pain is a vertebral compression fracture in which a weakened or injured vertebral body loses height or collapses. The weakening of the vertebral body may be due to acute injury or, more often, degenerative changes such as osteoporosis. The compression fractures often appear on lateral radiographs as wedge deformities with greater loss of height anteriorly. FIG. 1 is a representation of a vertebra having a compression fracture with loss of anterior height of the vertebral body.

A vertebral augmentation procedure is a treatment modality in which the height of the vertebral body is elevated or restored, and stabilized at the elevated or restored height. One manner of doing so is a kyphoplasty procedure in which the height of the vertebral body is restored with an expandable member such as a balloon. The balloon expands to create a cavity within the interior of the vertebral body by compressing and displacing the cancellous bone. Curable material may be delivered into the cavity and interdigitate with the surrounding cancellous bone to cure and stabilize the vertebral body.

Another manner of restoring height of the vertebral body includes deploying an implant. The implant is configured to expand to elevate or restore the height of the vertebral body. In addition to providing for less disruption of the trabeculae relative to the radially-expanding balloon, the implant may remain within the vertebral body to enhance and maintain structural integrity of the vertebral body at the elevated or restored height. The curable material may be delivered in and/or around the implant and interdigitate with the surrounding cancellous bone to cure and stabilize the implant within the vertebral body. An exemplary implant and system for doing so is described in commonly owned U.S. Pat. Nos. 7,846,206 and 8,986,386, among others, entire contents of which are hereby incorporated by reference, and sold under the tradename SpineJack by Vexim SAS (Balma, France).

As implied by its name, the SpineJack implant includes at least two pairs of supports configured to move upper and lower plates in the caudiocranal direction in a scissor jack fashion. As a result, a maximum extent by which the implants may be deployed is a based on a length of the supports, and the length of the supports may be based on an overall length implant itself. The overall length of the implant may be constrained by anatomy, for example, a distance between the anterior cortical rim and the pedicle through which the implant is inserted. Consequently, in certain situations, it may be desirable for the implant to provide for increased expansion, and/or it may be desirable for the implant to expand by a given amount while reducing the overall length of the implant. In other words, it may be desirable for the implant to provide for a greater expansion-to-length ratio. Thus, while the SpineJack advantageously treats compression fractures and sequelae, there is further need in the art for an implant for restoring height of the vertebral body.

SUMMARY

An implant for restoring height of a vertebral body. The implant is configured to be deployed in the craniocaudal direction within the vertebral body after being directed through an access cannula with an introducer device. An upper plate and a lower plate are arranged parallel to one another and respectively form upper and lower loadbearing surfaces for the vertebral body, and a distal end portion and a proximal end portion positioned opposite the upper and lower plates. The implant includes a first support disposed between the upper and lower plates. The first support includes a distal end coupled to the distal end portion and a proximal end coupled to the upper plate. The implant further includes a second support disposed between the upper and lower plates. The second support comprising a proximal end coupled to the proximal end portion and a distal end coupled to the upper plate. The proximal end of the first support is coupled to the upper plate at an axial position closer to the proximal end portion than an axial position where the distal end of the second support is coupled to the upper plate.

An implant for restoring height of a vertebral body. An upper plate and a lower plate respectively form first and second loadbearing surfaces for the vertebral body. The implant is configured to be directed through an access cannula in an insertion configuration in which the upper and lower plates are spaced apart at a first distance, and expanded to a deployed configuration in which the upper and lower plates are moved away from one another in a craniocaudal direction to a second distance greater than the first distance. Each of the upper and lower plates are substantially parallel to a longitudinal axis of the implant that extends in a proximal-to-distal direction. The implant includes a first pair of supports coupled to the upper plate and disposed between the upper and lower plates. The first pair of supports are arranged in a crisscross configuration in the proximal-to-distal direction in each of the insertion configuration and the deployed configuration.

An implant for restoring height of a vertebral body. The implant is configured to be deployed in the craniocaudal direction within the vertebral body after being directed through an access cannula with an introducer device. An upper plate and a lower plate respectively form upper and lower loadbearing surfaces for the vertebral body. Each of the upper and lower plates are substantially parallel to a longitudinal axis of the implant that extends in a proximal-to-distal direction. The implant includes a distal end portion and a proximal end portion positioned opposite the upper and lower plates and each defining coaxial bores. The implant further includes opposing lateral pairs of supports disposed between the upper and lower plates and spaced apart from one another on opposing sides of a plane extending through the upper and lower plates and extending through the longitudinal axis in the proximal-to-distal direction. A retaining element extends through the implant between the opposing lateral pairs of supports. The retaining element is configured to deploy the implant and retain the implant after deployment.

An implant for restoring height of a vertebral body. An upper plate and a lower plate respectively form upper and lower loadbearing surfaces for the vertebral body. The implant is configured to be directed through an access cannula in an insertion configuration in which the upper and lower plates are spaced apart at a first distance, and expanded to a deployed configuration in which the upper and lower plates are moved away from one another in a craniocaudal direction to be spaced apart at a second distance greater than the first distance. Each of the upper and lower plates are substantially parallel to a longitudinal axis of the implant in the insertion and deployed configurations. The implant includes a distal end portion and a proximal end portion positioned opposite the upper and lower plates. The implant further includes a first support, a second support, a third support, and a fourth support. The first support coupled to the distal end portion and the upper plate. The second support is coupled to the proximal end portion and the upper plate. The third support is coupled to the distal end portion and the lower plate. The fourth support is coupled to the proximal end portion and the lower plate. The first and fourth supports are arranged substantially parallel to one another in each of the insertion configuration and the deployed configuration. The second and third supports are arranged substantially parallel to one another in each of the insertion configuration and the deployed configuration.

An implant for restoring height of a vertebral body. An upper plate and a lower plate respectively form first and second loadbearing surfaces for the vertebral body. The implant configured to be directed through an access cannula in an insertion configuration in which the upper and lower plates are spaced apart at a first distance, and expanded to a deployed configuration in which the upper and lower plates are moved away from one another in a craniocaudal direction to a second distance greater than the first distance. Each of the upper and lower plates are substantially parallel to a longitudinal axis of the implant that extends in a proximal-to-distal direction. The implant includes a distal end portion and a proximal end portion positioned opposite the upper and lower plates in the insertion configuration. The implant further includes a pair of supports coupled to the upper plate and disposed between the upper and lower plates. The first pair of supports are arranged to intersect, in each of the insertion configuration and the deployed configuration, a plane perpendicular to the longitudinal axis that bifurcates the implant between the distal end and proximal end portions.

An implant for restoring height of a vertebral body. The implant configured to be deployed in the craniocaudal direction within the vertebral body after being directed through an access cannula with an introducer device. An upper plate and a lower plate are arranged parallel to one another and respectively form upper and lower loadbearing surfaces for the vertebral body. The implant includes a distal end portion and a proximal end portion positioned opposite the upper and lower plates. The implant further includes a first support and a second support disposed between the upper and lower plates. The first support includes a distal end coupled to the distal end portion and a proximal end coupled to the upper plate. The second support includes a distal end coupled to the distal end portion and a proximal end coupled to the upper plate. An upper support fork is positioned between the upper and lower plates and comprising a distal end coupled to the upper plate and a pair of supports coupled to the proximal end portion.

An implant for restoring height of a vertebral body. An upper plate and a lower plate respectively forming first and second loadbearing surfaces for the vertebral body. The implant configured to be directed through an access cannula in an insertion configuration in which the upper and lower plates are spaced apart at a first distance, and expanded to a deployed configuration in which the upper and lower plates are moved away from one another in a craniocaudal direction to a second distance greater than the first distance. Each of the upper and lower plates are substantially parallel to a longitudinal axis of the implant that extends in a proximal-to-distal direction. The implant includes a distal end portion and a proximal end portion positioned opposite the upper and lower plates. The implant further includes a first support disposed between the upper and lower plates. The first support comprising a distal end coupled to the distal end portion and a proximal end coupled to the upper plate. An upper support fork is positioned between the upper and lower plates and comprising a distal end coupled to the upper plate and a pair of supports coupled to the proximal end portion. The first support and the pair of supports of the upper support fork are arranged in a crisscross configuration in the proximal-to-distal direction in each of the insertion configuration and the deployed configuration.

An implant for restoring height of a vertebral body. An upper plate and a lower plate respectively form first and second loadbearing surfaces for the vertebral body. The implant is configured to be directed through an access cannula in an insertion configuration in which the upper and lower plates are spaced apart at a first distance, and expanded to a deployed configuration in which the upper and lower plates are moved away from one another in the craniocaudal direction to a second distance greater than the first distance. Each of the upper and lower plates are substantially parallel to a longitudinal axis of the implant that extends in a proximal-to-distal direction. The upper plate and the lower plate have a fixed length. The implant includes a distal end portion and a proximal end portion positioned opposite the upper and lower plates. The implant further includes a first support coupled to the upper plate and the distal end portion, and a second support coupled to the lower plate and the proximal end portion. The first support and the second support have a fixed length with the fixed lengths of the first and second supports being within the range of approximately 50-90% of the fixed length of the upper and lower plates.

BRIEF DESCRIPTION OF THE DRAWINGS

Advantages of the present invention will be readily appreciated as the same becomes better understood by reference to the following detailed description when considered in connection with the accompanying drawings.

DETAILED DESCRIPTION

Figure 1:
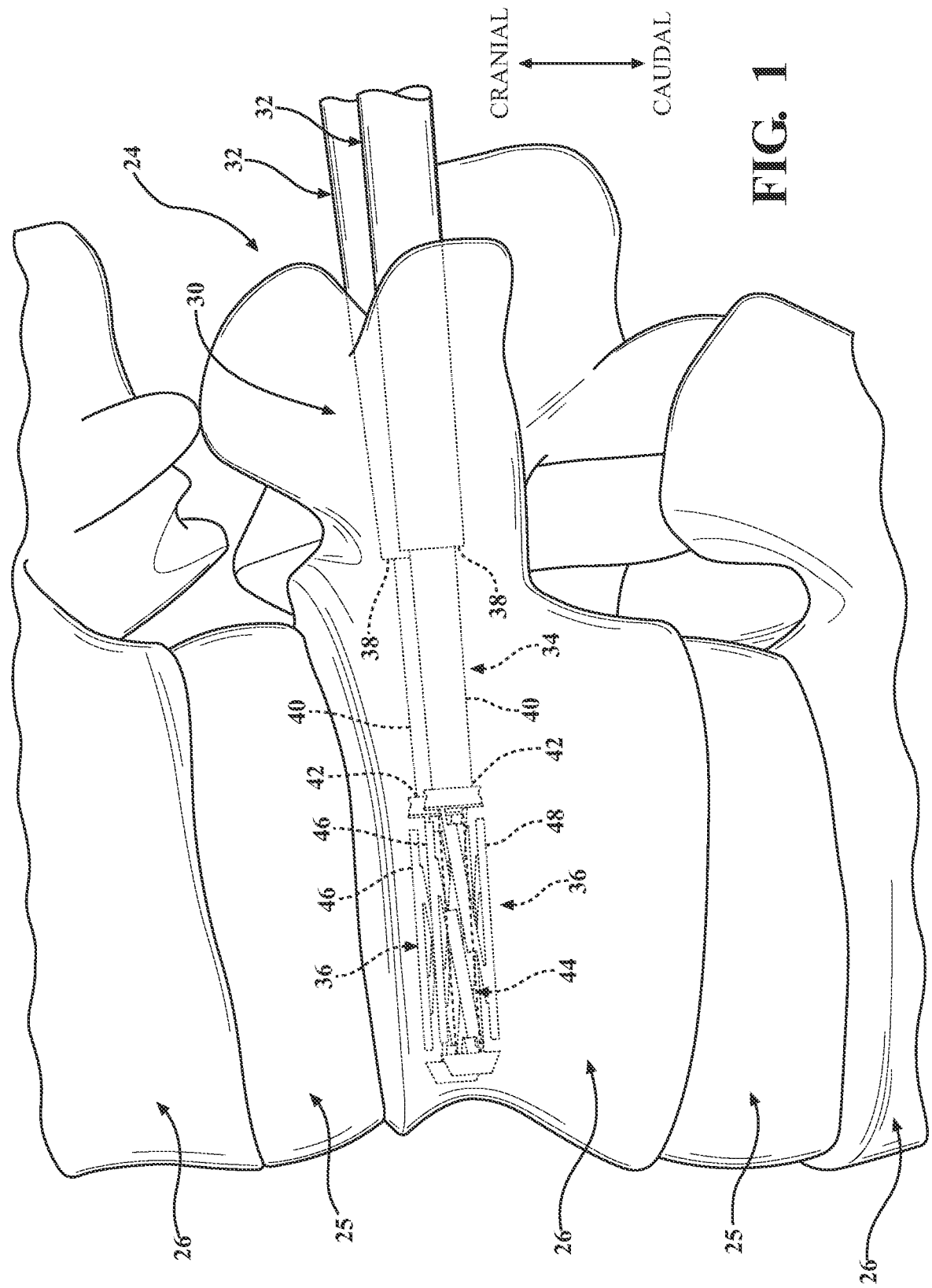
FIG. 1 is an illustration of a portion of the spine showing three vertebrae separating by two intervertebral discs. A system including an implant is shown positioned within an interior region of a vertebral body of one of the vertebrae. The implant is in an insertion configuration.
Figure 2:
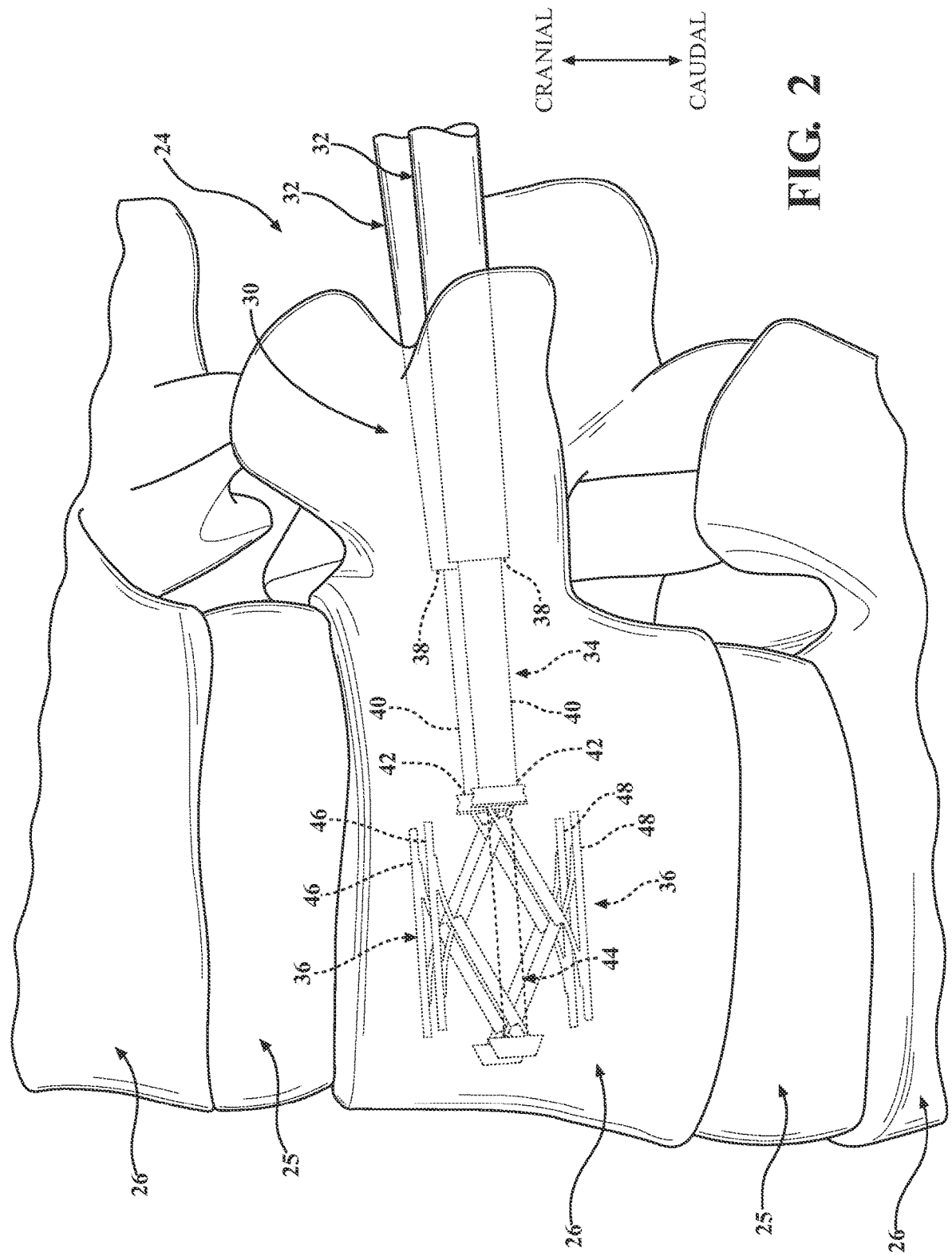
FIG. 2 is an illustration of the portion of the spine of FIG. 1 with the implant shown in a deployed configuration.

FIGS. 1 and 2 are illustrations of a portion of the spine showing three vertebrae 24 separating by two intervertebral discs 25. Each of the vertebrae 24 includes a vertebral body 26 defining an interior region having cancellous bone. FIG. 1 further shows one of the vertebral bodies having loss of height anteriorly, for example, from a compression fracture, resulting in a wedge-shaped deformity. With reference to FIGS. 1, 2, 4 and 13, the anatomical directions may also be referenced in accordance with standard medical convention; i.e., cranial towards the head of patient or upwardly, caudal towards the feet of the patient or downwardly, distal towards an end of the device inserted first into the patient (or away from the practitioner), and proximal towards the practitioner.

A system 30 for restoring height of the vertebral body 26 may include an access cannula 32, an introducer device 34, and an implant 36, 136. FIG. 1 shows the implant 36 in an insertion configuration within the vertebral body 26, and FIG. 2 shows the implant 36 in a deployed configuration that augments the vertebral body 26 having an elevated or restored height in a manner to be described. With the vertebral body 26 at the restored height, endplates of the vertebral body 26 are spaced farther apart from one another than in the unrestored height, which may reduce or eliminate pain and other sequelae associated with the compression fracture.

The access cannula 32 includes a distal end 38 configured to be directed through the pedicle to access the interior region of the vertebral body 26. A trocar (not shown) may include a solid shaft sized to be snugly and removably disposed within the access cannula 32 as the access cannula 32 is directed through the pedicle. The trocar may include a length slightly greater than a length of the cannula such that a sharp tip of the trocar pierces the cortical bone of the pedicle, and the trocar prevents coring of tissue within a lumen of the access cannula 32. Once the distal end 38 of the access cannula 32 is positioned within the vertebral body 26, for example as shown in FIGS. 1 and 2, the trocar is removed. The access cannula 32 provides a working channel to within the interior region of the vertebral body 26 along an axis. The inner diameter of the access cannula 32 is at least sufficient to receive the introducer device 34 and the implant 36, 136 in the insertion configuration. A cavity creator (not shown) may be directed through the working channel to within the vertebral body 26. The cavity creator may be operated (e.g., rotated) to create a generally cylindrical cavity within the cancellous bone with the cavity being approximate to the size of the implant 36, 136 in the insertion configuration.

The introducer device 34 includes an elongate shaft 40 having a distal end 42. FIGS. 1 and 2 show the distal end 42 may be coupled to the implant 36, and more particularly to a retaining element 44 of the implant 36 to be described, in a generally coaxial arrangement. Opposite the distal end 42, the introduce device 34 may include a handle 41 and an actuator 43 (see FIGS. 11 and 20) configured to receive an input of the user to move the implant 36 from the insertion configuration of FIG. 1 to the deployed configuration of FIG. 2. An exemplary operation of the introducer device 34 and its interfacing with the retaining element 44 of the implant 36 is described in commonly owned U.S. Pat. Nos. 8,986,386 and 9,414,933, the entire contents of which are hereby incorporated by reference. In procedures utilizing a bipedicular approach, the workflow is repeated through the contralateral pedicle, which is reflected in FIGS. 1 and 2 showing two systems 30 deploying two implants 36 within the same vertebral body 26. Alternatively, a unipedicular approach may include utilizing a singular system 30 with a singular implant 36.

Figure 11:
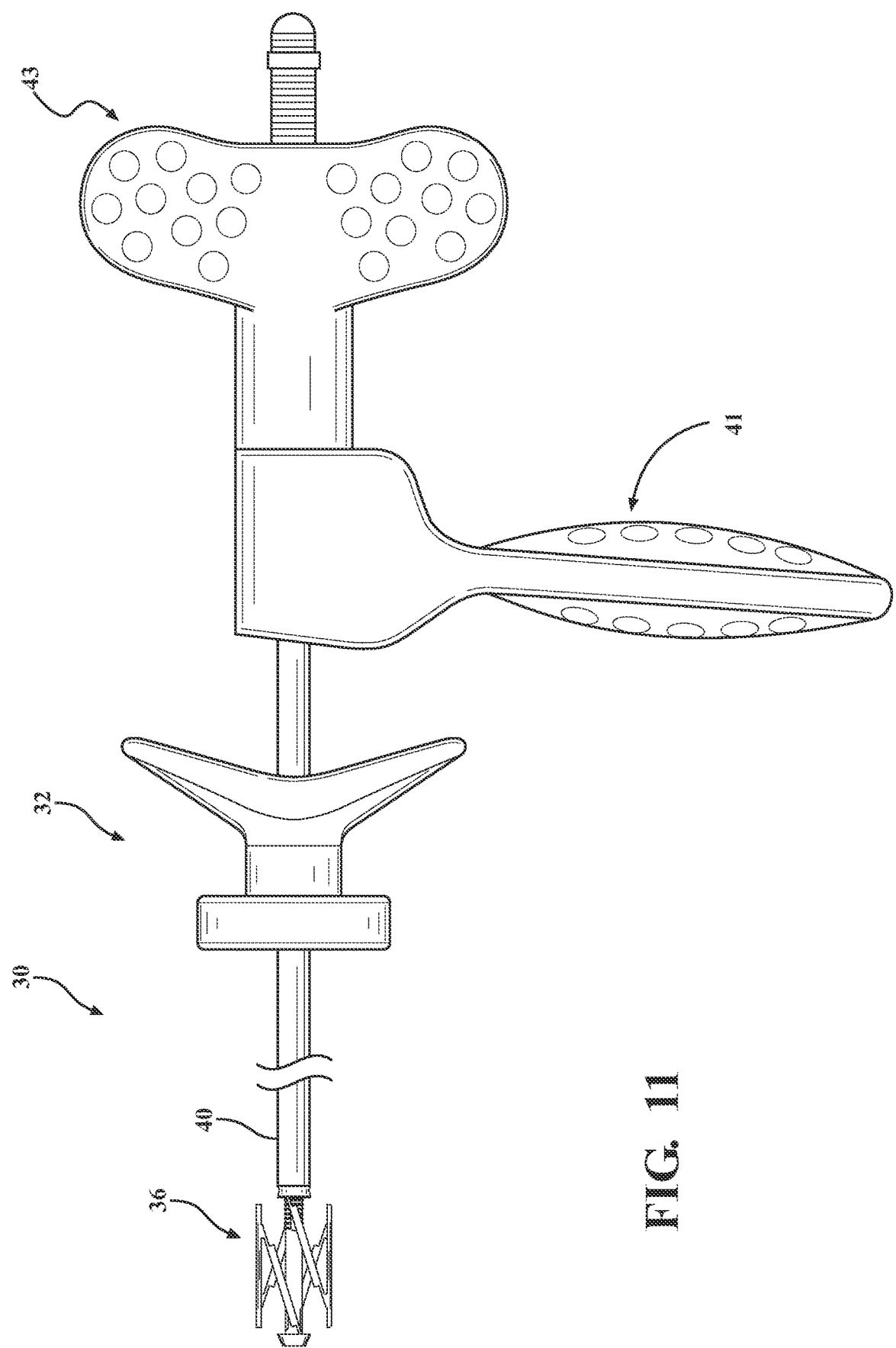
FIG. 11 is an elevation view of a system including the implant of FIG. 4 with the introducer device actuated to deploy the implant.
Figure 12:
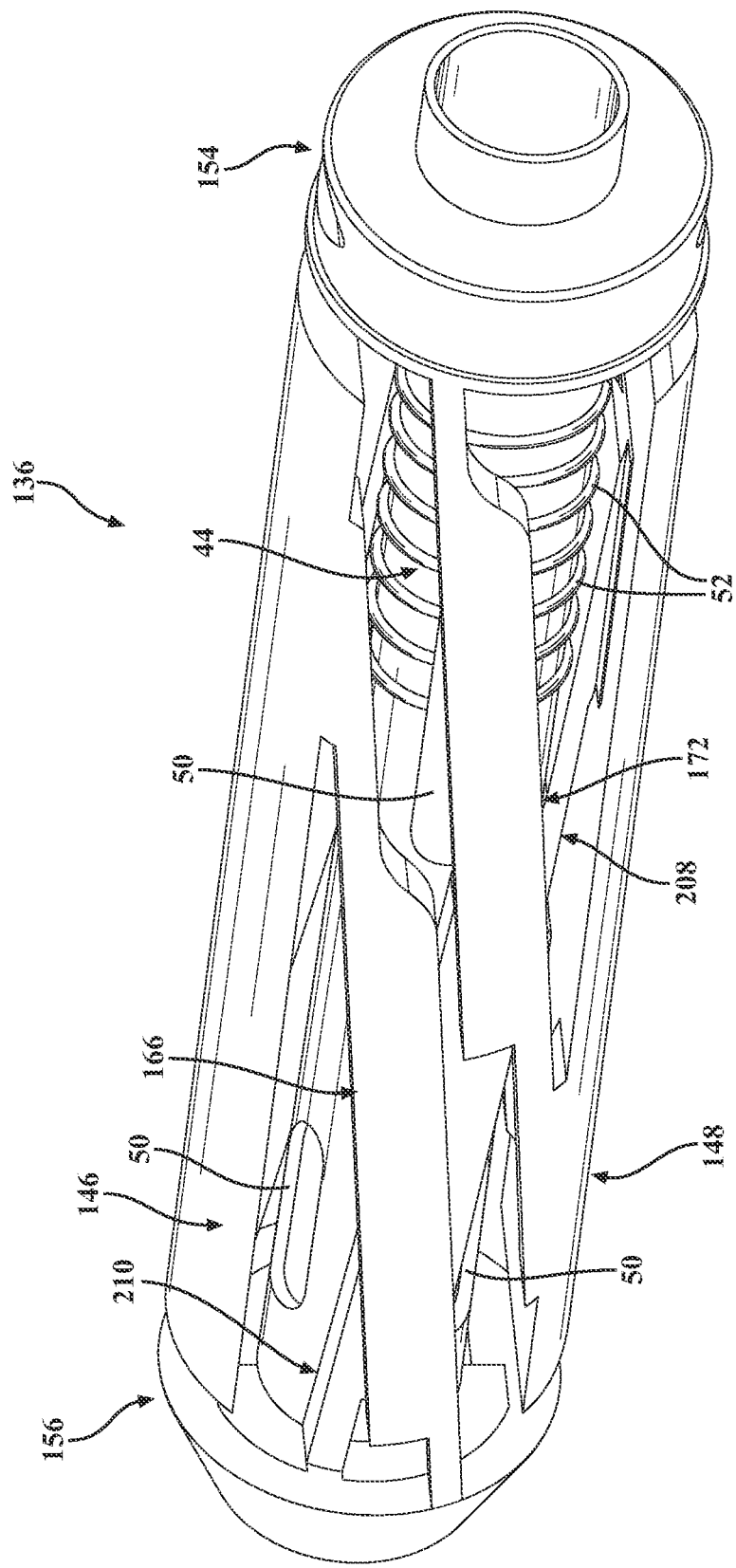
FIG. 12 is a perspective view of another implant.
Figure 13:
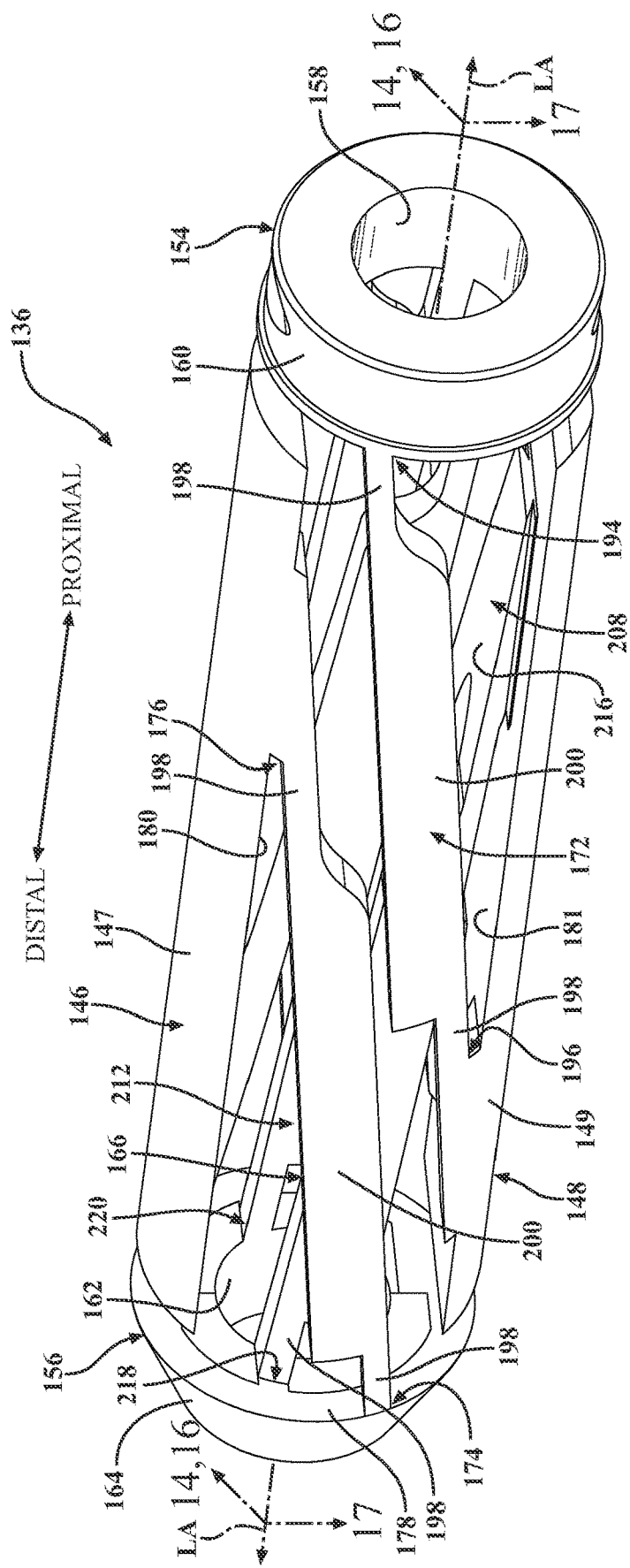
FIG. 13 is a perspective view of the implant of FIG. 12 with a retaining element of the implant removed.
Figure 20:
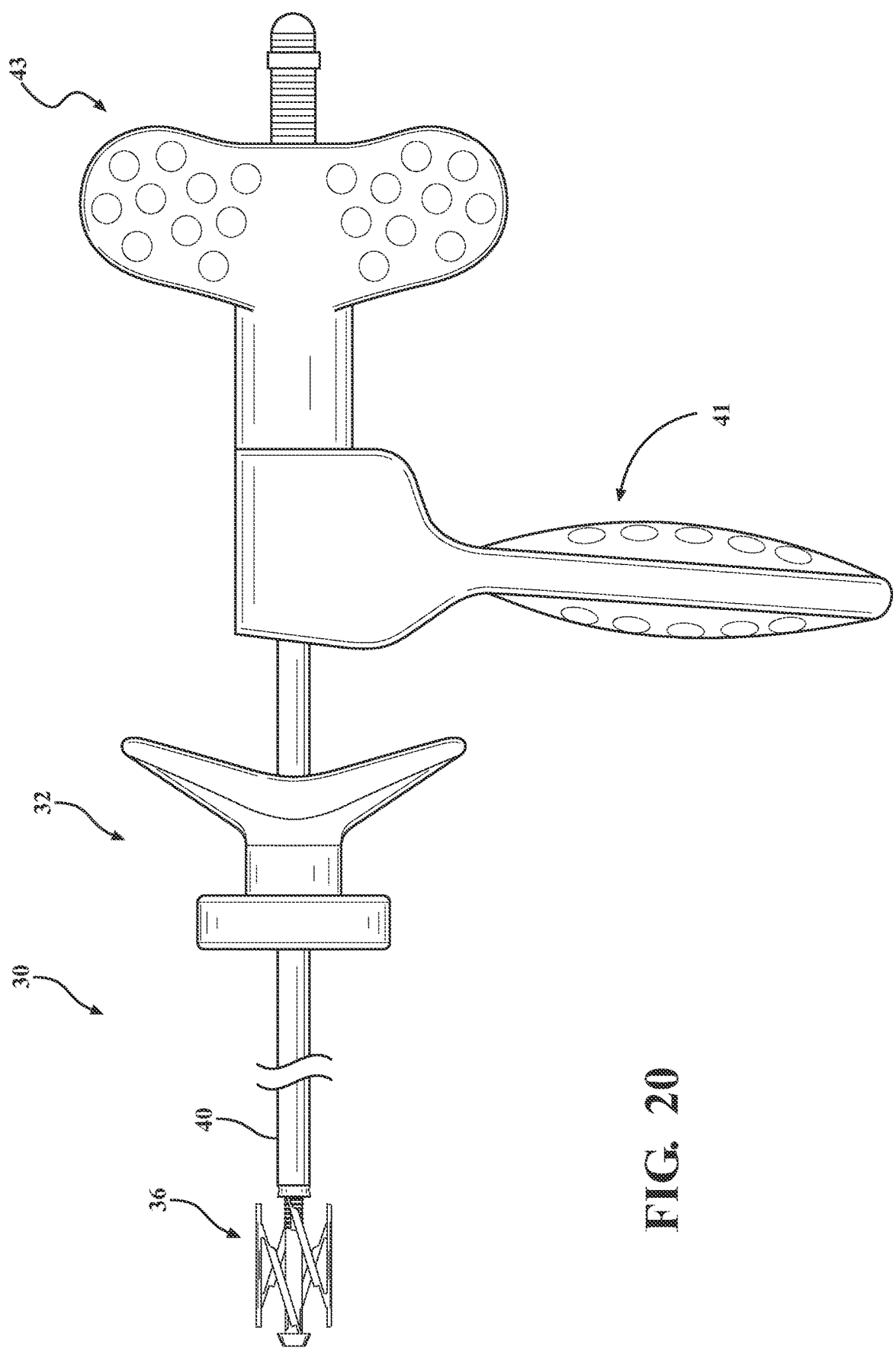
FIG. 20 is an elevation view of a system including the implant of FIG. 13 with the introducer device actuated to deploy the implant.
Figure 21A:
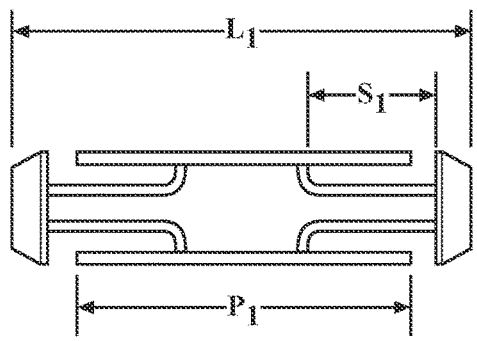
FIGS. 21A-21D are schematic representations of a known implant and a schematic representation of the implants of FIGS. 3 and 12 in each of the insertion configuration and the deployed configuration.
Figure 21B:
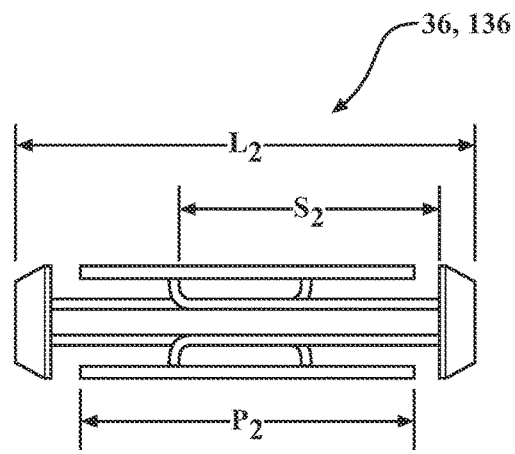
Figure 21C:
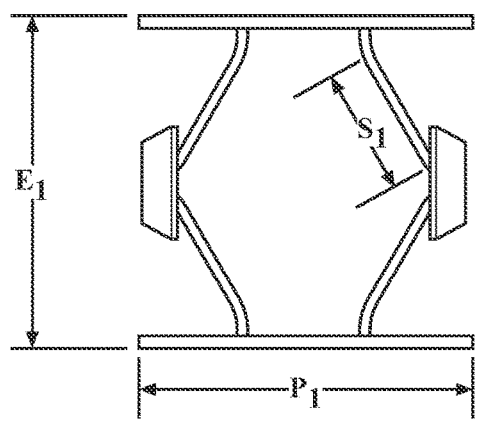
Figure 21D:
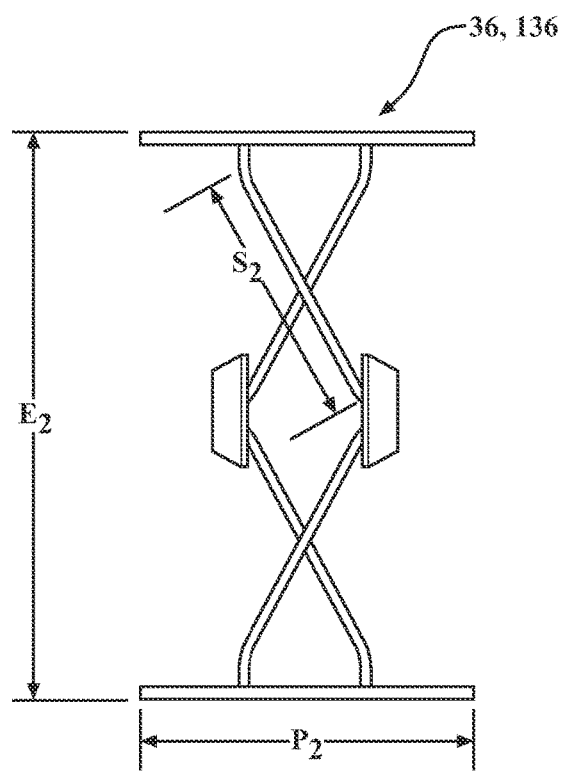

Operation of the introducer device 34 moves the upper and lower plates 46, 146, 48, 148 away from one another in the craniocaudal direction to restore the height of the vertebral body 26, in effect moving the implant 36, 136 from the insertion configuration to the deployed configuration shown in FIGS. 11 and 20. The upper and lower plates 46, 146, 48, 148 may be arranged parallel to one another and respectively form upper and lower loadbearing surfaces 47, 147, 49, 149 for the vertebral body 26. As the upper and lower plates 46, 146, 48, 148 are moved away from one another, the upper and lower plates 46, 146, 48, 148 compress adjacent cancellous bone and move endplates of the vertebral body 26 away from one another to the elevated or restored height. Locking features 52 on the retaining element 44 engage complementary locking features (not shown) on a proximal end portion 54, 154 of the implant 36, 136 to facilitate maintaining the implant 36, 136 in the deployed configuration that has been selectively tuned by the practitioner. In other words, the deployed configuration may include the upper and lower plates 46, 146, 48, 148 being spaced apart from one another by any distance greater than that an initial distance in the insertion configuration, up to and include a maximum distance that is based on lengths of the supports to be described. The complimentary locking features 52 facilitate maintaining the spacing between the upper and lower plates 46, 146, 48, 148 at the desired distance.

With the implant 36, 136 in the deployed configuration, an inner shaft of the introducer device 34 may be removed. A delivery device having curable material may be coupled to and/or directed through the elongate shaft 40 of the introducer device 34 in communication with a lumen of the retraining element 44. The retaining element 44 includes one or more apertures 50 in communication with the lumen such that the curable material exits the aperture(s) 50 and into the vertebral body 26. The curable material interdigitates the implant and the surrounding cancellous bone to cure and stabilize or fix the implant 36, 136 within the vertebral body 26. The elongate shaft 40 of the introducer device 34 is removed and the implant 36, 136 remains fixed within the vertebral body 26 with the vertebral body 26 at the elevated or restored height. As reflected above, the workflow may be performed using the implant 36 of FIGS. 3-11 and/or the implant 136 of FIGS. 12-20 to be described in turn.

Figure 3:
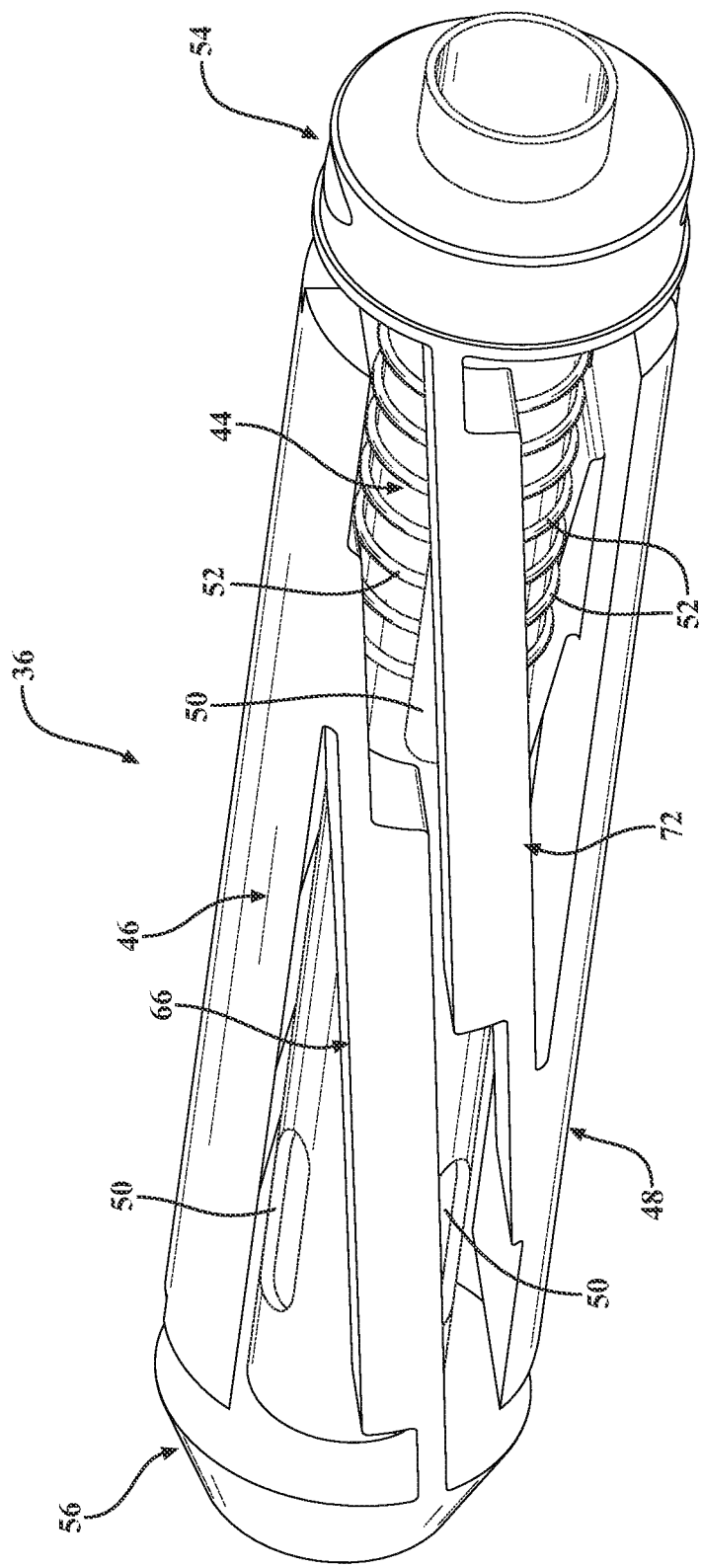
FIG. 3 is a perspective view of an implant.
Figure 4:
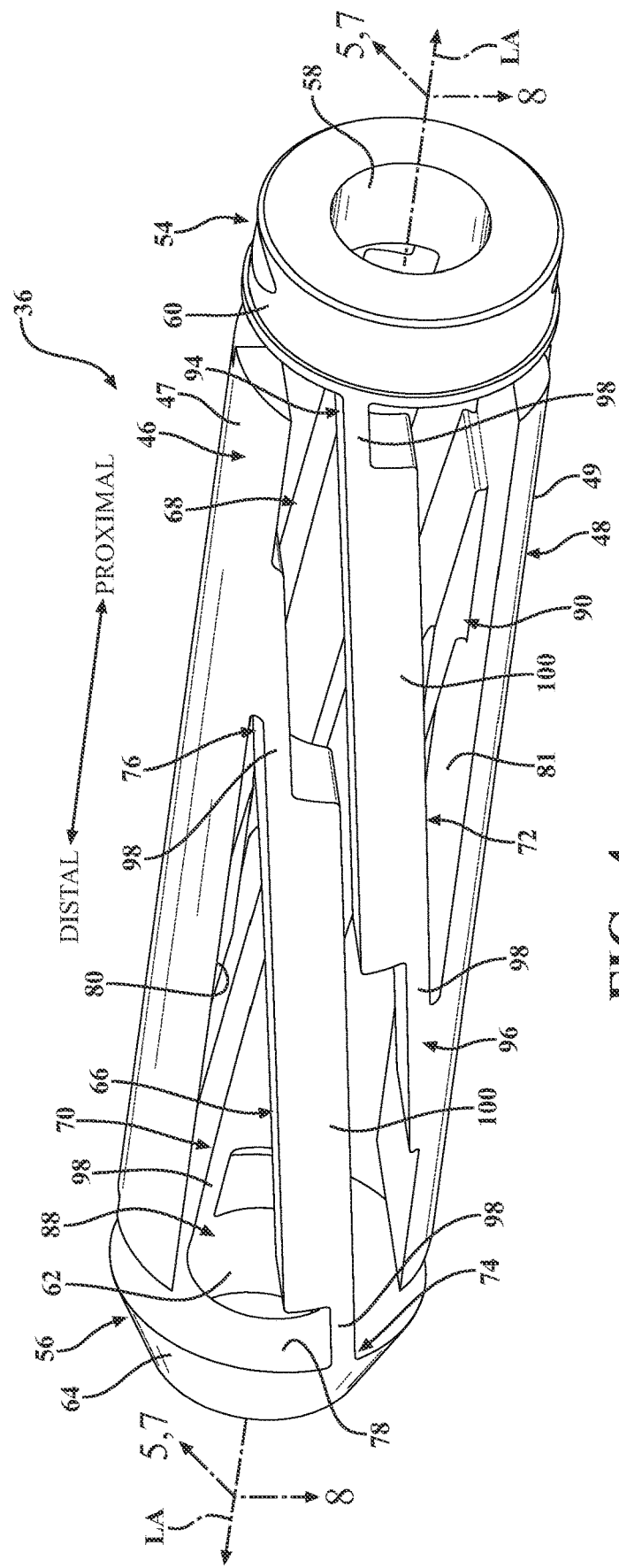
FIG. 4 is a perspective view of the implant of FIG. 3 with a retaining element of the implant removed.
Figure 5:
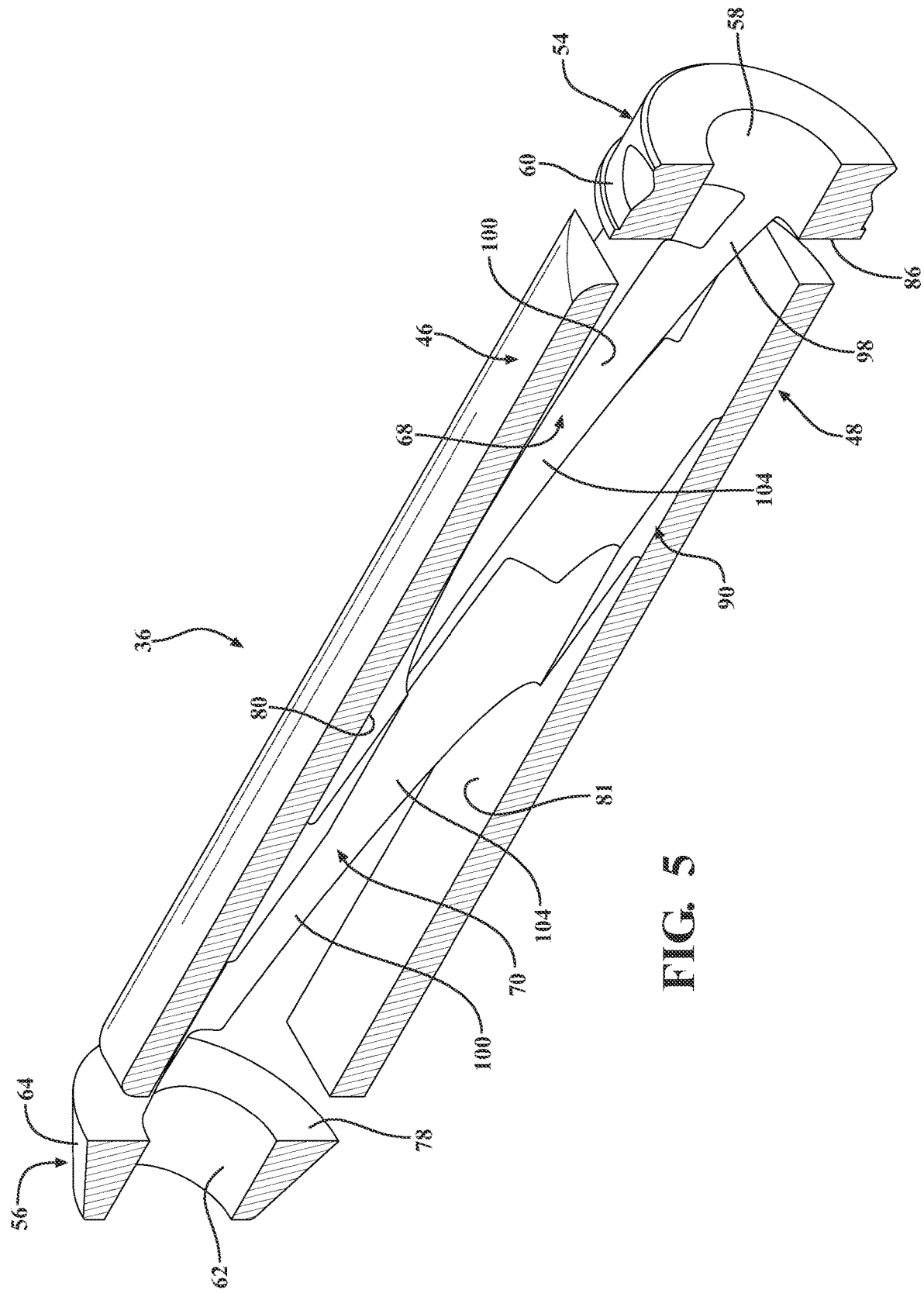
FIG. 5 is a sectional view of the implant of FIG. 4 taken along lines 5-5.

Referring now to FIGS. 3-11, the implant 36 includes the proximal end portion 54, and a distal end portion 56 opposite the proximal end portion 54. In particular, the proximal end portion 54 and the distal end portion 56 are positioned opposite the upper and lower plates 46, 48. The proximal end portion 54 may include an inner surface defining a bore 58, and an outer surface 60 opposite the inner surface. FIG. 4 best shows the proximal end portion 54 being a ring member that is cylindrical in shape. The bore 58 may be coaxial with the longitudinal axis (LA) of the implant 36. The distal end portion 56 may include an inner surface defining a bore 62, and an outer surface 64 opposite the inner surface. The outer surface 64 of the distal end portion 56 may be tapered to facilitate insertion of the implant 36 through the cancellous bone. The bore 62 may be coaxial with the longitudinal axis of the implant 36, and further coaxial with the bore 58 of the proximal end portion 54. As shown in FIG. 3, the bores 58, 62 may be sized to receive the retaining element 44.

Figure 6:
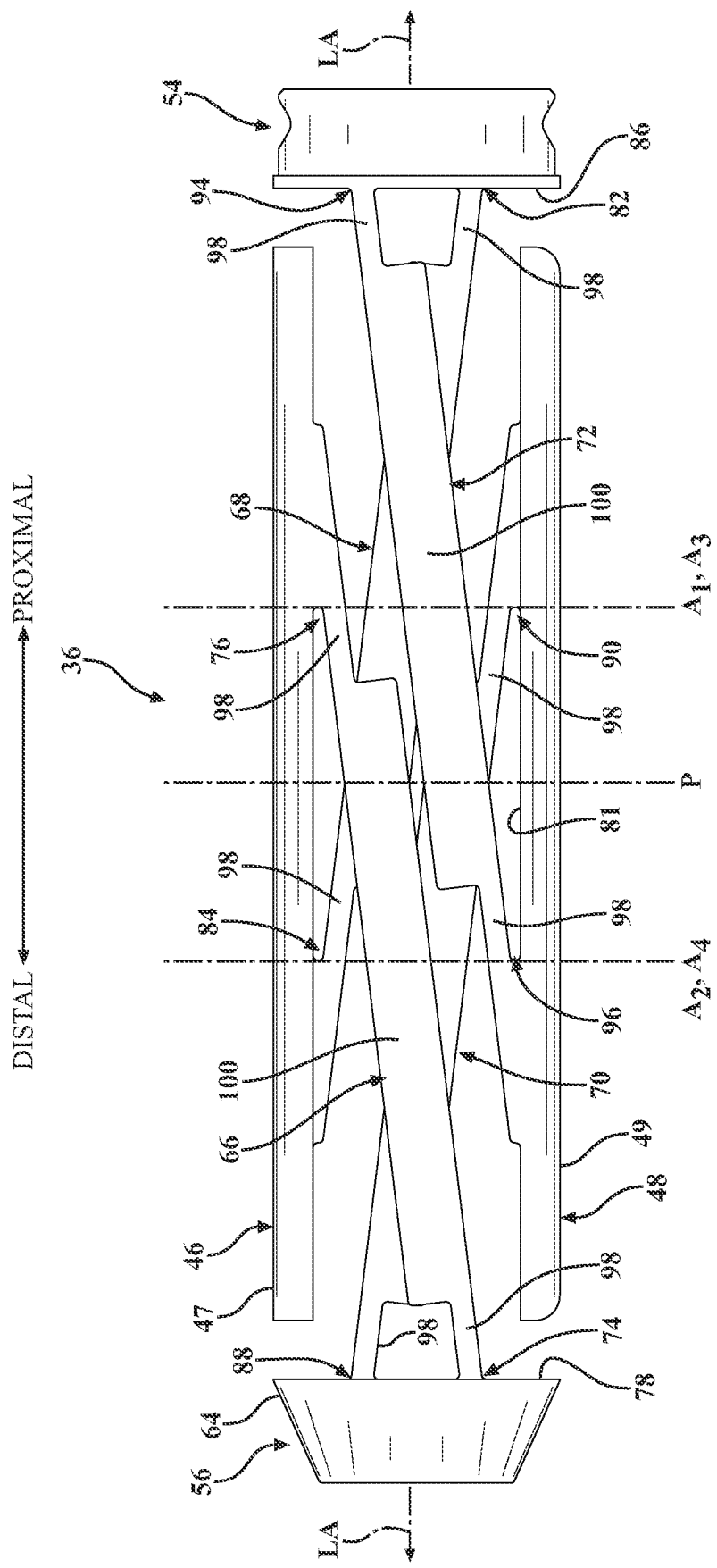
FIG. 6 is an elevation view of the implant of FIG. 4.
Figure 7:
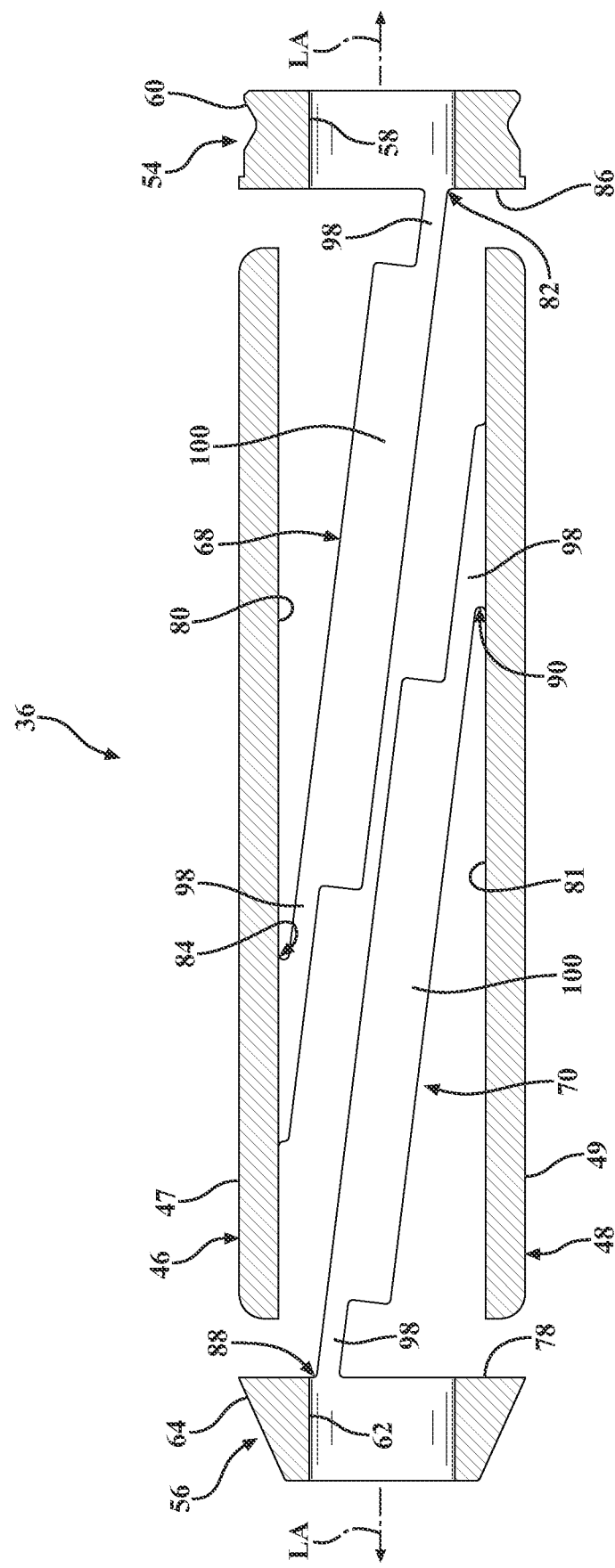
FIG. 7 is a sectional view of the implant of FIG. 4 taken along lines 7-7.

With particular reference to FIGS. 4, 6, 8 and 9, the implant 36 includes a first support 66 and a second support 68 each disposed between the upper and lower plates 46, 48. The first and second supports 66, 68 may be disposed between the proximal end portion 54 and the distal end portion 56 with the implant 36 in the insertion configuration. In a broadest sense, the first and second supports 66, 68 (along with third and fourth supports 70, 72, if applicable) provide a framework for the implant 36 in the insertion and deployed configurations, and further bear the forces on the upper and lower loadbearing surfaces 47, 49 of the upper and lower plates 46, 48, respectively, when the implant 36 is in the deployed configuration within the vertebral body 26. The first support 66 includes a distal end 74 coupled to the distal end portion 56, and a proximal end 76 coupled to the upper plate 46. More particularly, the distal end 74 is coupled to an inner surface 78 of the distal end portion 56, and the proximal end 76 is coupled to an underside 80 of the upper plate 46 opposite the upper loadbearing surface 47. FIG. 4 shows the first support 66 as being an elongate structure having a length greater than a width and a thickness. As best shown in FIG. 7, the second support 68 includes a proximal end 82 coupled to the proximal end portion 54 and a distal end 84 coupled to the upper plate 46. More particularly, the proximal end 82 is coupled to an inner surface 86 of the proximal end portion 54, and the distal end 84 is coupled to the underside 80 of the upper plate 46. The second support 68 may be an elongate structure having a length greater than a width and a thickness.

The proximal end 76 of the first support 66 is coupled to the upper plate 46 at an axial position closer to the proximal end portion 54 than an axial position where the distal end 84 of the second support 68 is coupled to the upper plate 46. In other words and with reference to FIG. 6, the axial position (i.e., in the proximal-to-distal direction) where the first support 66 is coupled to the upper plate 46 is defined as axis $A_1$, and the axial position where the second support 68 is coupled to the upper plate 46 is identified as axis $A_2$. The axis $A_2$ is distal to the axis $A_1$. Stated more simply, the first and second supports 66, 68 are arranged in a crisscross configuration in the proximal-to-distal direction when viewed in elevation. As a result and to be further explained in detail, the implant 36 advantageously provides for a greater expansion-to-length ratio. Stated differently, for a given length of the implant 36, the upper and lower plates 46, 48 are capable of being moved apart in the caudiocranal direction by a greater distance than known implants. The practical benefits are readily appreciated and at least two-fold: (i) in procedures in which the height of the vertebral body 26 is to be restored by a previously achievable amount with known implants, an implant having a smaller length may be used, and (ii) previously unobtainable amounts of restoration of the height of the vertebral body 26 are achievable for a given constraint of the anatomy, as previously mentioned.

The third support 70 and the fourth support 72 are disposed between the upper and lower plates 46, 48. The third and fourth supports 70, 72 may be disposed between the proximal end portion 54 and the distal end portion 56 with the implant 36 in the insertion configuration. The third support 70 includes a distal end 88 coupled to the distal end portion 56, and a proximal end 90 coupled to the lower plate 48. More particularly, the distal end 88 is coupled to the inner surface 78 of the distal end portion 56, and the proximal end 90 is coupled to an upper side 81 of the lower plate 48. FIG. 7 shows the third support 70 as being an elongate structure having a length greater than a width and a thickness. The fourth support 72 includes a proximal end 94 coupled to the proximal end portion 54 and a distal end 96 coupled to the lower plate 48. More particularly, the proximal end 94 is coupled to the inner surface 86 of the proximal end portion 54, and the distal end 96 is coupled to the upper side 81 of the lower plate 48. The fourth support 72 may be an elongate structure having a length greater than a width and a thickness.

The proximal end 90 of the third support 70 is coupled to the lower plate 48 at an axial position closer to the proximal end portion 54 than an axial position where the distal end 96 of the fourth support 72 is coupled to the lower plate 48. In other words and with reference to FIG. 6, the axial position where the third support 70 is coupled to the lower plate 48 is defined as axis $A_3$, and the axial position where the fourth support 72 is coupled to the lower plate 48 is identified as axis $A_4$. The axis $A_4$ is distal to the axis $A_3$. The third and fourth supports 70, 72 are arranged in a crisscross configuration in the proximal-to-distal direction when viewed in elevation. Owing the crisscross configurations described above, it readily follows that the proximal end of the first support 66 is coupled to the upper plate 46 at an axial position closer to the proximal end portion 54 than an axial position of where the distal end 96 of the fourth support 72 is coupled to the lower plate 48, and the distal end 84 of the second support 68 is coupled to the upper plate 46 at an axial position closer to the distal end portion 56 than an axial position of where the proximal end 88 of the third support 70 is coupled to the lower plate 48.

The first, second, third, and/or fourth support 66, 68, 70, 72 may include material webs 98 comprising reduced thickness portions configured to plastically deform as said implant 36 is deployed within the vertebral body 26. With reference to the figures generally, each the first, second, third, and fourth supports 66, 68, 70, 72 includes a strut portion 100 and the material webs 98 positioned on one side or opposing sides of the strut portion 100. A thickness of the strut portion 100 is greater than the thickness of the material webs 98 such that, as the implant 36 is moved from the insertion configuration to the deployed configuration, stresses are localized to impart bending of the material webs 98. Further, the material webs 98 may be considered to define the aforementioned proximal and distal ends of the respective supports. For example, FIG. 4 shows the first support 66 having two material webs 98, one associated with the distal end 74 where the first support 66 couples with the distal end portion 64, and another associated with the proximal end 76 where the first support 66 couples with the upper plate 46. Owing to the relative thicknesses of the material webs 98 of the first support 66 and the strut portion 100 of the first support 66, and further owing to the retaining element 44 constraining the proximal and distal end portions 54, 56, the material webs 98 bend and plastically deform as the upper and lower plates 46, 48 are moved apart from one another. The effect is articulation of the first support 66 relative to each of the distal end portion 56 and the upper plate 46, in the present example. The above described behavior is present in the material webs 98 of each of the second, third, and fourth supports 68, 70, 72. Further disclosure regarding the structure and function of the material webs 98 is disclosed in the aforementioned U.S. Pat. Nos. 7,846,206 and 8,986,386.

Figure 8:
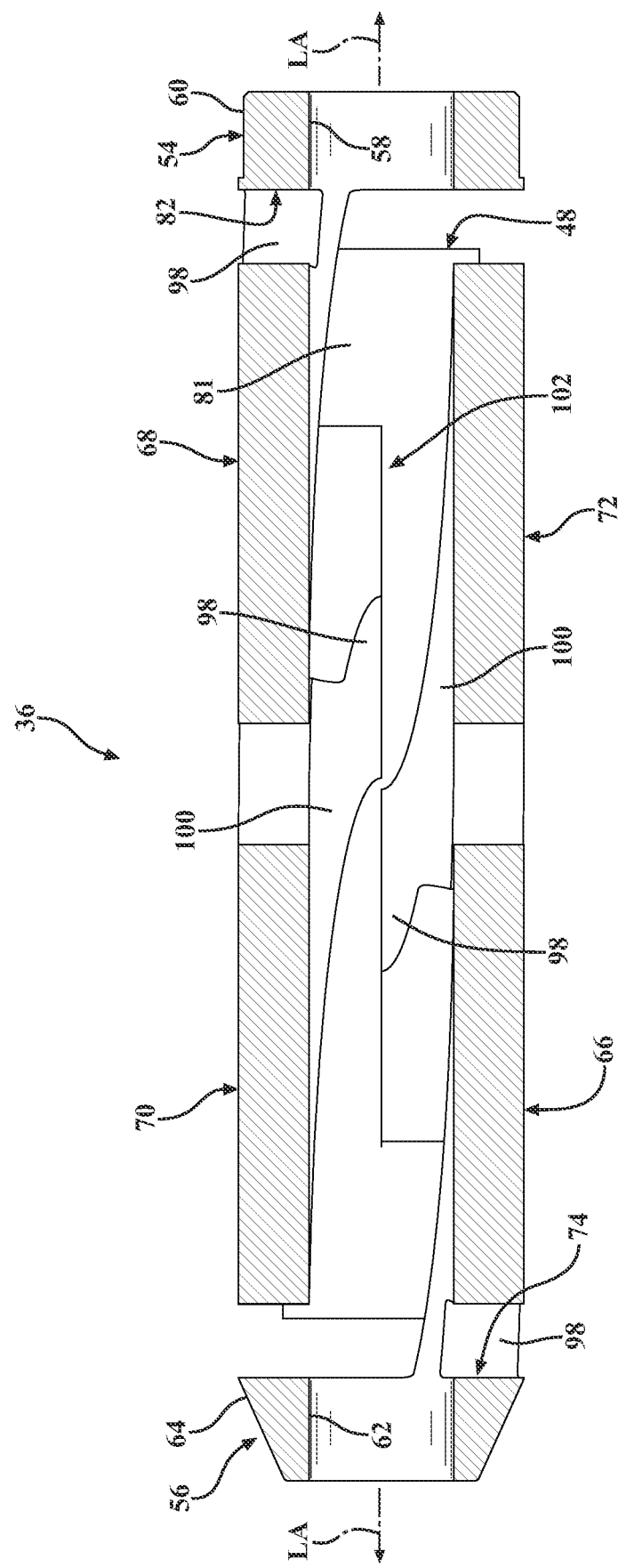
FIG. 8 is a sectional view of the implant of FIG. 4 taken along lines 8-8.

Referring now to FIG. 8 showing a top plan view of the implant 36 in section, the first support 66 and the fourth support 72 are spaced apart laterally from the second support 68 and the third support 70. In other words, the first and third supports 66, 70 may be considered an opposing lateral pair of supports, and the second and fourth supports 68, 72 may be considered another opposing lateral pair of supports. For convention, lateral spacing may be considered to be disposed on opposing sides of a plane extending through the upper and lower plates 46, 48 and extending through the longitudinal axis in the proximal-to-distal direction. The lateral spacing of the first and third supports 66, 70 from the second and fourth supports 68, 72 defines a void space 102. With concurrent reference to FIGS. 9 and 10, the void space 102 is in communication with the bores 58, 62 defined by the proximal and distal end portions 54, 56. The retaining element 44 is at least partially disposed in the void space 102 as generally appreciated from FIG. 3.

The retaining element 44 may be a cylindrical stem extending through the bores 58, 62 and the void space 102. As a result, the bores 58, 62 and the first, second, third, and fourth supports 66, 68, 70, 72 may collectively define a generally cylindrical shaped channel extending through the implant 36 in the proximal-to-distal direction. Each of the first, second, third, and fourth supports 66, 68, 70, 72 may include an arcuate inner surface 104. The arcuate inner surface 104 may be on the material webs 98 and/or the strut portions 100 of each of the first, second, third, and fourth supports 66, 68, 70, 72. The arcuate inner surfaces 104 collectively defining the void space 102 having a generally cylindrical profile. The cylindrical profile may complementary to the bores 58, 62 of the proximal and distal end portions 54, 56.

Figure 9:
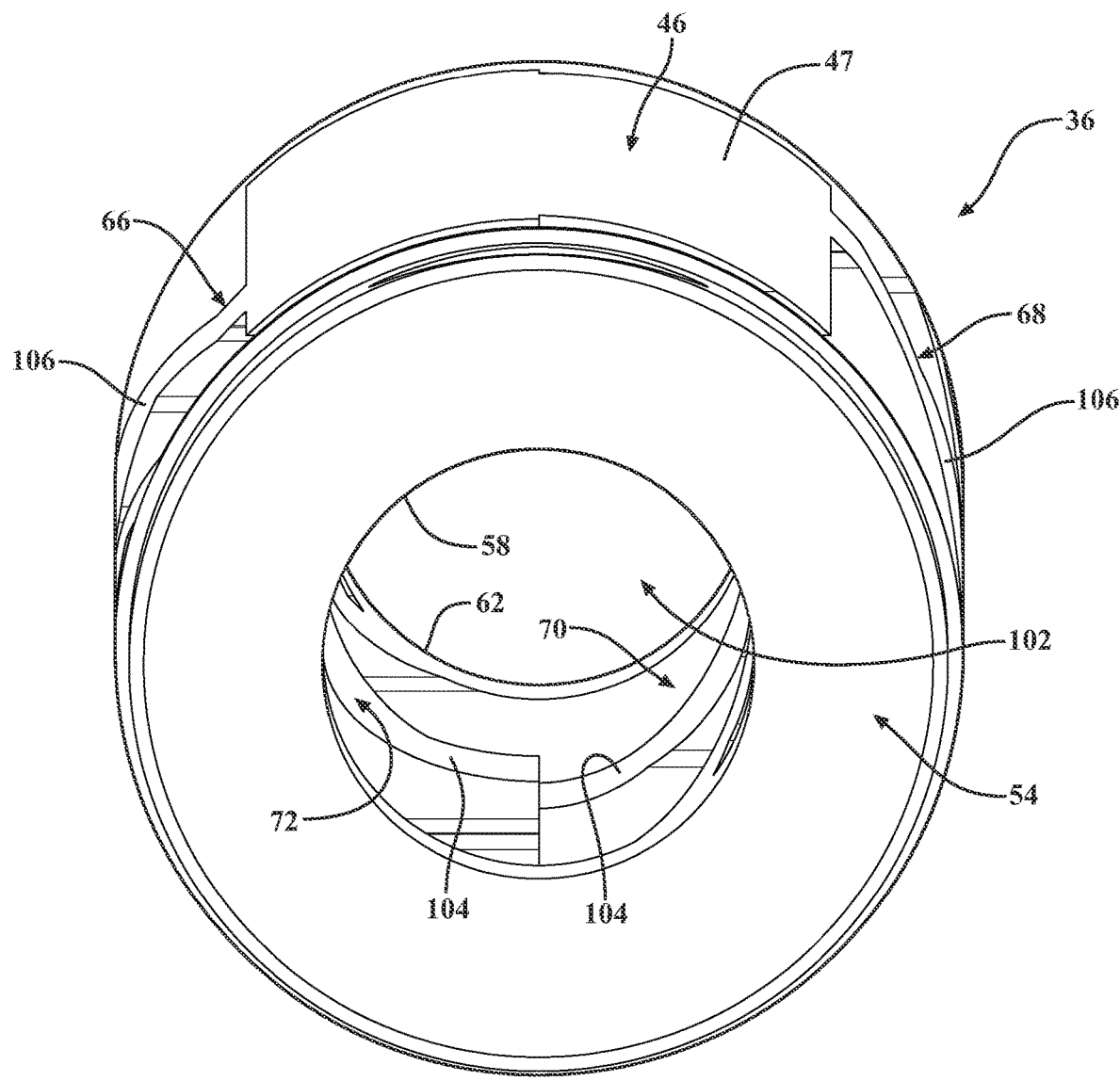
FIG. 9 is an axial upper perspective view of the implant of FIG. 4.
Figure 10:
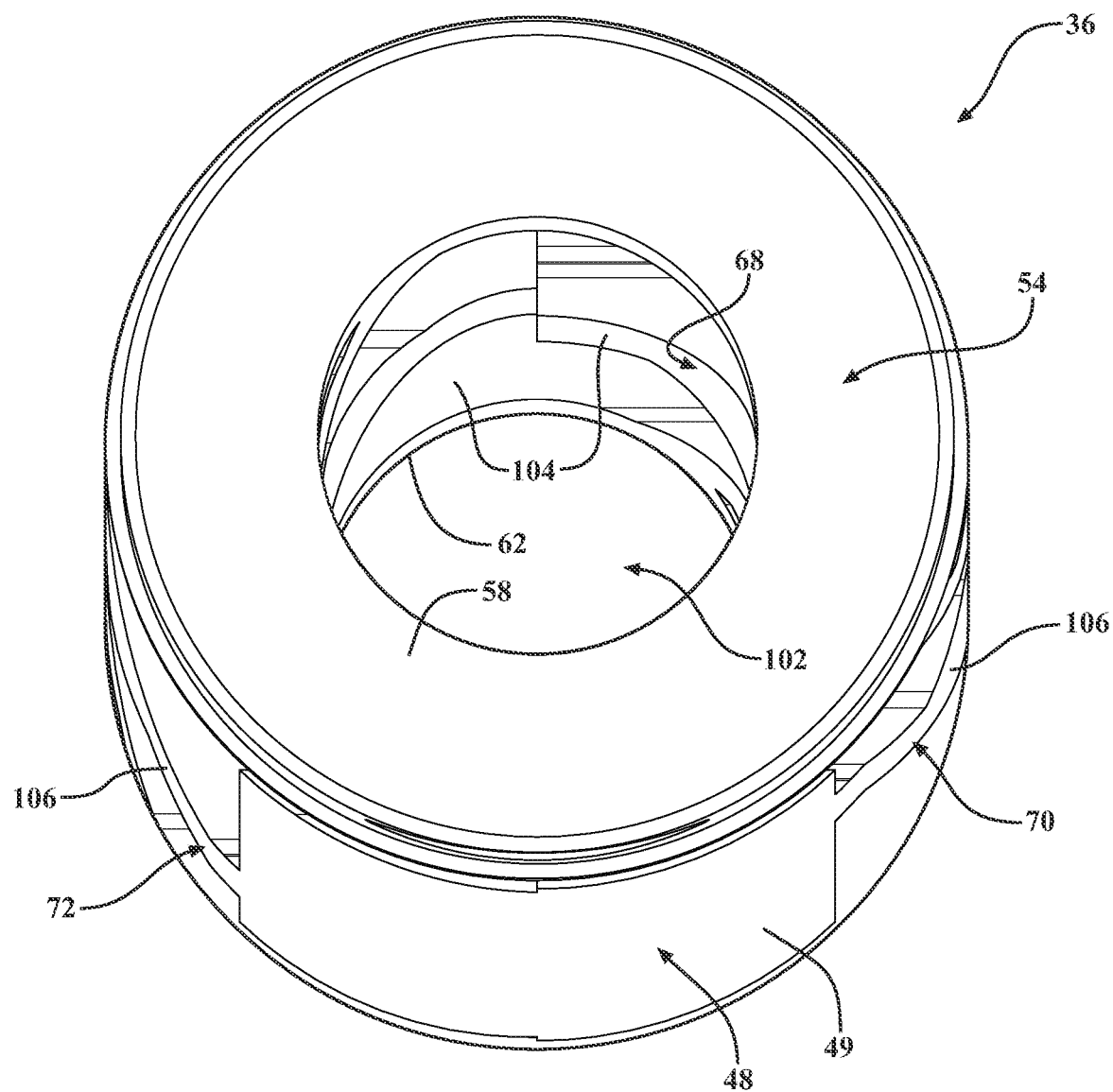
FIG. 10 is an axial lower perspective view of the implant of FIG. 4.

Each of the first, second, third, and fourth supports 66, 68, 70, 72 may further include an arcuate outer surface 106 opposite said arcuate inner surface 104. The arcuate inner surface 104 may be on the material webs 98 and/or the strut portions 100. As best shown in FIGS. 9 and 10, the load-bearing surfaces 47, 49 of the upper and lower plates 46, 48 may be arcuate in shape with the arcuate shapes complementing the arcuate outer surfaces 106 of the first, second, third, and fourth supports 66, 68, 70, 72. The arcuate surfaces provide the implant 36 with a generally cylindrical outer profile. The cylindrical outer profile may have an outer diameter approximate to an outer diameter of the outer surfaces 60, 64 of the proximal and distal end portions 54, 56. The arrangement advantageously permits the implant 36 to be deployed through the shaft 40 of the introducer device 34 having a tubular shape.

As mentioned, the first and second supports 66, 68 and the third and fourth supports 70, 72 are arranged in the crisscross configuration in the proximal-to-distal direction when viewed in elevation. The first and second supports 66, 68 and the third and fourth supports 70, 72 are arranged in the crisscross configuration with the implant 36 in each of the insertion configuration and the deployed configuration. Referring to FIG. 6 showing the implant 36 in the insertion configuration, the first and second supports 66, 68 are arranged to intersect a plane (P) perpendicular to the longitudinal axis LA that bifurcates the implant 36 between the proximal and distal end portions 54, 56. With concurrent reference to FIG. 11 showing the implant 36 in the deployed configuration, the first and second supports 66, 68 are arranged to intersect the plane. Likewise, the third and fourth supports 70, 72 may be arranged to intersect the plane in each of the insertion and deployed configurations. Owing to the arrangement of the first, second, third, and fourth supports 66, 68, 70, 72, the first and fourth supports 66, 72 may be substantially parallel to one another in the insertion and the deployed configurations, and the second and third supports 68, 70 may be substantially parallel to one another in the insertion and the deployed configurations. FIG. 6 shows the first and fourth supports 66, 72 parallel to one another in the insertion configuration, and FIG. 7 shows the second and third supports 68, 70 parallel to one another in the insertion configuration. FIG. 11 shows the first and fourth supports 66, 72 as well as the second and third supports 68, 70 parallel to one another in the deployed configuration.

Achieving the crisscross arrangement(s) and the desired motion in which the upper and lower plates 46, 48 are substantially parallel to one another in the insertion and deployed configuration requires a unique design, especially in view of the constraint providing the generally cylindrical profile of the implant 36. For example, providing the crisscrossing supports on the same lateral side of the implant 36 is not particularly feasible in view of the aforementioned constrains to have a small form factor to be deployed through the introducer device 34 often having a lumen of less than six millimeters (mm). The implant 36 of the present disclosure overcomes the aforementioned technical challenges. The crisscrossing supports are positioned on opposite lateral sides of the implant 36. The results is a unique arrangement: (i) the first support 66 on a first lateral side is directly connected to the upper plate 46 and the distal end portion 56, but not directly connected to the lower plate 48 or the proximal end portion 54; (ii) the second support 68 on a second lateral side is directly connected to the lower plate 48 and the distal end portion 56, but not directly connected to the upper plate 46 or the proximal end portion 54; (iii) the third support 50 on the second lateral side is directly connected to the upper plate 46 and the proximal end portion 54, but not directly connected to the lower plate 48 or the distal end portion 56; and (iv) the fourth support 72 on the first lateral side is directly connected to the lower plate 48 and the proximal end portion 54, but not directly connected to the lower plate 48 or the distal end portion 56. The arrangement provides the aforementioned framework in which the implant 36 provides for a greater expansion-to-length ratio while accommodating the retaining element 44 in a small form factor having a generally cylindrical profile.

FIG. 21 schematically illustrates an example of the increased expansion achievable with the implants 36, 136 of the present disclosure. The left of FIG. 21 shows a schematic representation of a known implant, for example, the Spine-Jack implant includes at least two pairs of supports configured to move upper and lower plates in the caudiocranal direction in a scissor jack fashion. A length of the implant is identified as $l_1$, a length of a support is identified as $S_1$, and a length of a plate is identified as $p_1$. The right side of FIG. 21 shows a schematic representation of the implant 36, 136 of the present disclosure. A length of the implant 36, 136 is identified as $l_2$, a length of a support is identified as $S_2$, and a length of a plate is identified as $p_2$. In the illustrated example, $l_1$ is equal to $l_2$ and $p_1$ is equal to $p_2$, and thus the overall implants generally have the same dimensions. The crisscross configuration(s) of the supports of the implant 36, 136, however, result in the support $S_2$ being appreciably longer and resulting in significantly greater expansion $e_2$ in the deployed configuration than the expansion $e_1$ of the known implant. Similarly, to achieve the expansion $e_1$ of the known implant, the implant 36, 136 having a smaller implant length $l_2$ and plate length $p_2$ may be used. In one example, the known implant may have a support-to-plate ratio (i.e., $S_1/p_1$) of 10 mm:21 mm, or just below 50%. In certain implementations, the implant 36, 136 may have a support-to-plate ratio (i.e., $S_2/p_2$) of 16 mm:22 mm, or approximately 73%. In certain implementations, the implant 36, 136 may have a support-to-plate ratio (i.e., $S_2/p_2$) of 22 mm:28 mm, or approximately 79%. Other ratios are achievable and contemplated, for example, within the range of approximately 50-110%, more specifically within the range of approximately 60-85%, and even more specifically within the range of approximately 70-75%. Owing to this significant increase in the support-to-plate ratio, the increased expansion of the implant 36, 136 for a given length may be 1.25, 1.5, 1.75, 2.0, 2.5 and 3.0 or greater times than that of the known implant. In one example, the increased expansion of the implant 36, 136 for a given length may be approximately double. Again, based on the significant increase in the support-to-plate ratio, an implant having a smaller length may be used to achieve a given amount of height restoration, and previously unobtainable amounts of restoration of the height of the vertebral body 26 are achievable.

Still further, the increase in the support-to-plate ratio may provide for the largest possible surface to be supported on the upper and lower plates 46, 48, 146, 148 for a given length of length and expansion. The increase in size of the loadbearing surfaces 47, 147, 49, 149 of the upper and lower plates 46, 146, 48, 148 better accommodates the static and dynamic loads once the implant.

The framework of the implant 36, 136 may be comprised of biocompatible material, for example titanium or titanium alloy, and may be integrally formed. Owing to the crisscross configuration of the first and second supports 66, 68 and the third and fourth supports 70, 72, certain conventional manufacturing techniques may not be particularly suitable. For example, wire electrical discharge machining (EDM), in which rapidly recurring current discharges in a wire electrode removes material, may not be capable of accommodating the lateral profile (see FIG. 6) of the implant 36, 136. To overcome such manufacturing challenges, additive manufacturing may be particularly well suited for forming the framework of the implant 36, 136. The complex, overlapping structures along each of the principal axes of the implant 36, 136 may be realized through the additive manufacturing. Certain additive manufacturing techniques for orthopedic implants may be disclosed in United States Patent Publication Nos. 2017/0165790 and 2018/0353642, the entire contents of each are hereby incorporated by reference.

In addition to being well suited for forming the integral framework of the implant 36, 136, the use of additive manufacturing may provide additional advantages. As mentioned, each of the first, second, third, and fourth supports 66, 166, 68, 168, 70, 170, 72, 172 may include the arcuate outer surface 106, which may be difficult to fabricate as described without combining manufacturing techniques or additional finishing techniques. Likewise, the loadbearing surfaces 47, 147, 49, 149 of the upper and lower plates 46, 146, 48, 148 may be arcuate in shape, and the use of additive manufacturing may provide for an increase in size of these arcuate surfaces relative to, for example, the size achievable through conventional wire EDM. The increase in size of the loadbearing surfaces 47, 147, 49, 149 of the upper and lower plates 46, 146, 48, 148 better accommodates the static and dynamic loads once the implant 36, 136 is in situ.

Referring now to FIGS. 12-20, another implementation of the implant 136 is shown with like components relative to the previously described implant 36 identified with like numerals plus one hundred (100). Disclosure omitted relative to the implant 36 previously introduced is in the interest of brevity and is considered incorporated by reference. The implant 136 includes the upper plate 146, the lower plate 148, the proximal end portion 154 defining the bore 158, and the distal end portion 56 defining the bore 162.

The implant 136 includes the first support 166, the second support 168, the third support 170, and the fourth support 172 each disposed between the upper and lower plates 146, 148, and further disposed between the proximal and distal end portions 154, 156 in the insertion configuration. The first, second, third, and/or fourth supports 166, 168, 170, 172 may include the material webs 198 comprising reduced thickness portions configured to plastically deform as said implant 136 is deployed within the vertebral body 26. The first, second, third, and fourth supports 166, 168, 170, 172 includes the strut portion 200 and the material webs 198 positioned on one side or opposing sides of the strut portion 200.

Figure 16:
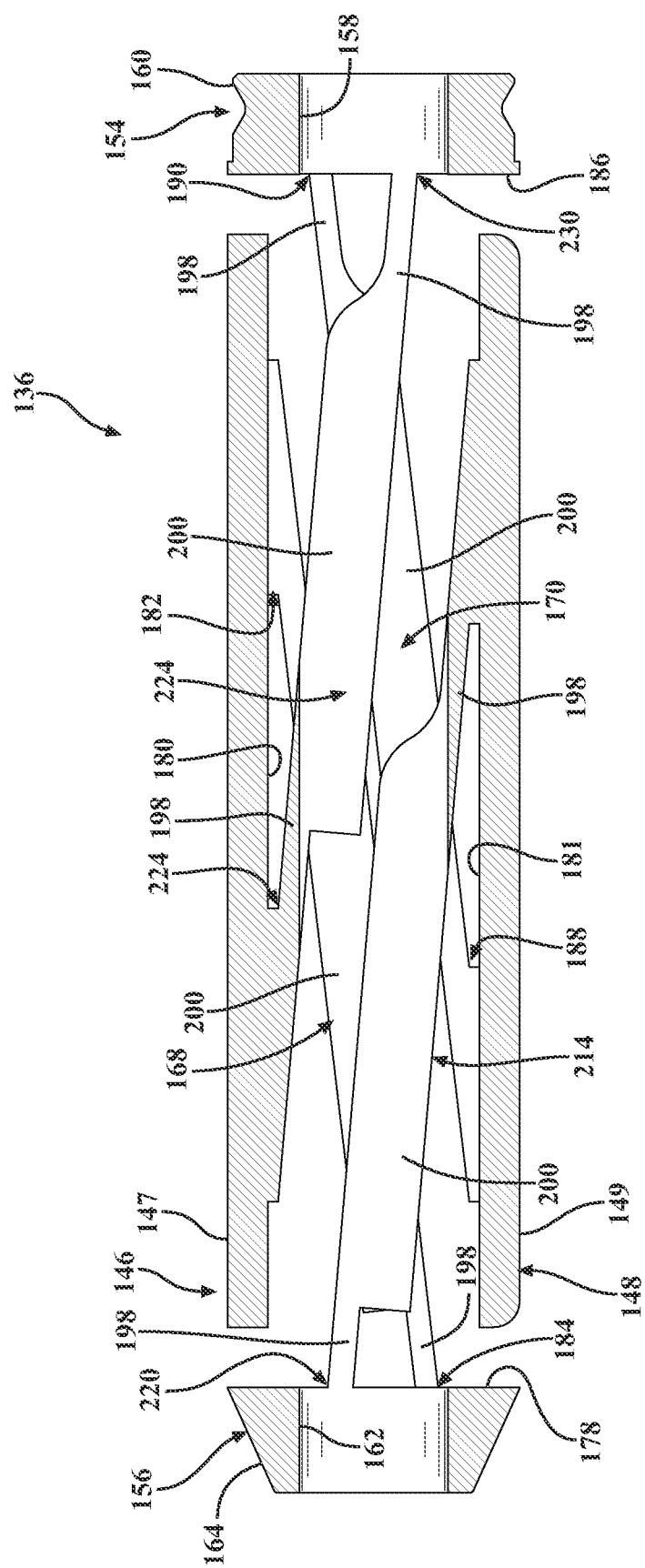
FIG. 16 is a sectional view of the implant of FIG. 13 taken along lines 16-16.

The first support 166 includes the distal end 174 coupled to the distal end portion 156, and the proximal end 176 coupled to the upper plate 146. As best shown in FIG. 16, the second support 168 includes the proximal end 182 coupled to the upper plate 146 and the distal end 184 coupled to the distal end portion 154. The proximal end 176 of the first support 166 is coupled to the upper plate 146 at least substantially the same axial position as where the proximal end 176 of the second support 168 is coupled to the upper plate 146. The third support 170 includes the distal end 188 coupled to the lower plate 148, and the proximal end 190 coupled to the proximal end portion 154. The fourth support 172 includes the proximal end 194 coupled to the proximal end portion 154 and the distal end 196 coupled to the lower plate 148. The distal end 188 of the third support 170 is coupled to the lower plate 148 at least substantially the same axial position as where the distal end 196 of the fourth support 172 is coupled to the lower plate 148.

Figure 15:
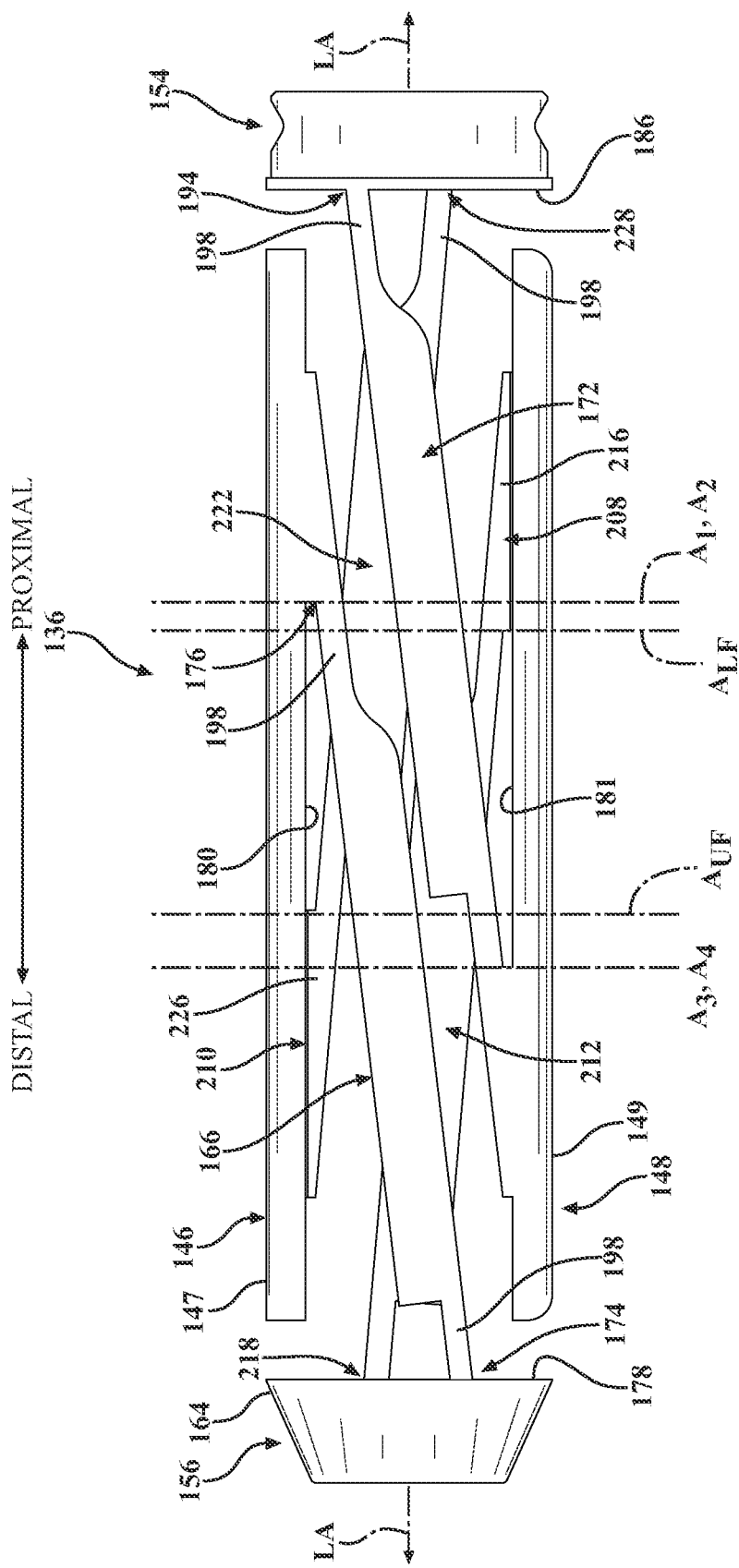
FIG. 15 is an elevation view of the implant of FIG. 13.
Figure 17:
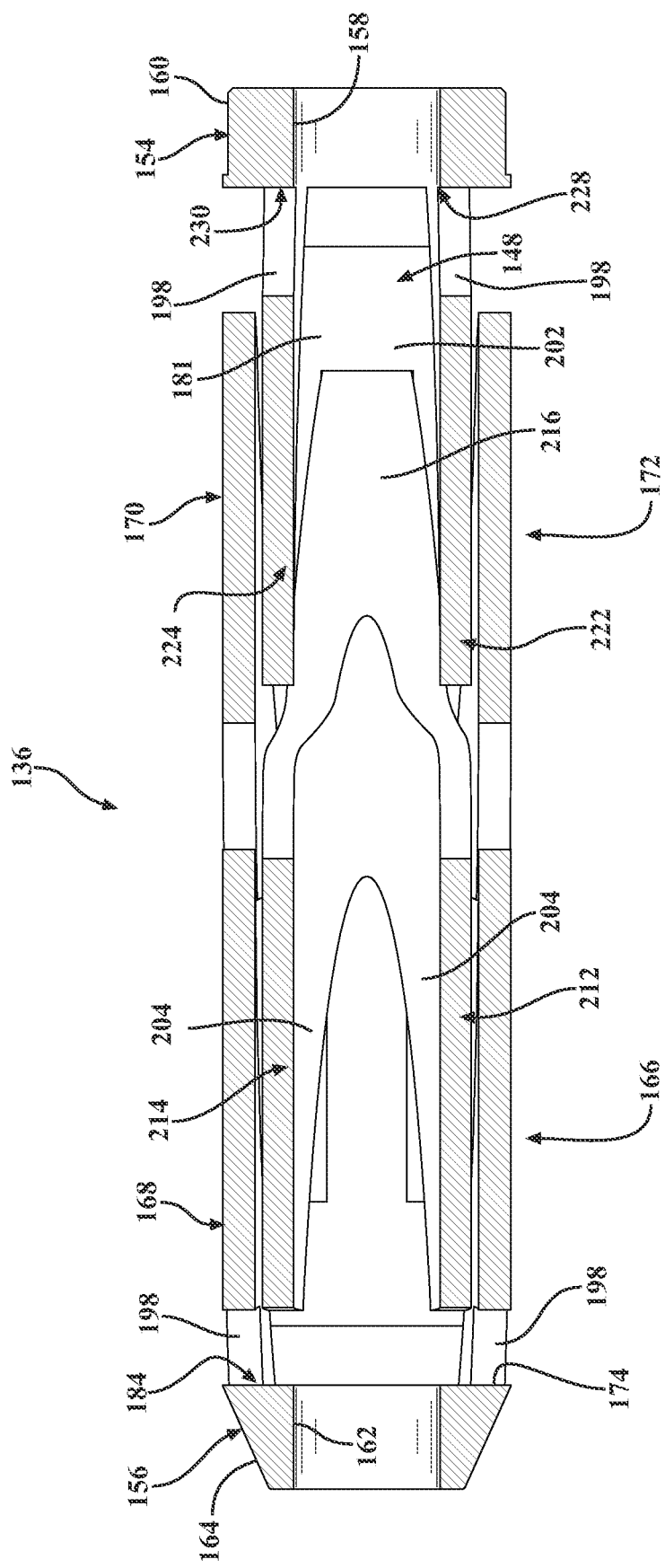
FIG. 17 is a sectional view of the implant of FIG. 13 taken along lines 17-17.

With particular reference to FIGS. 15 and 16, the first support 166 and the second support 168 may not crisscross, but rather be substantially parallel to and coplanar one another in the insertion and the deployed configurations. Likewise, the third and fourth supports 170, 172 may not crisscross, but be substantially parallel to and coplanar one another in the insertion and the deployed configurations. In certain implementations, the first, second, third, and fourth supports 166, 168, 170, 172 are substantially parallel to one another in the insertion and the deployed configurations. In other words, the first and third supports 166, 170 may be considered the opposing lateral pair of supports, and the second and fourth supports 168, 172 may be considered another opposing lateral pair of supports with the opposing lateral pairs of supports being mirrored relative to one another about a vertical plane extending through the longitudinal axis. FIG. 17 generally reflects this arrangement. However, it is contemplated that the first, second, third, and fourth supports 166, 168, 170, 172 may be arranged in a crisscross configuration in a manner similar to the implant 36 previously introduced.

Figure 14:
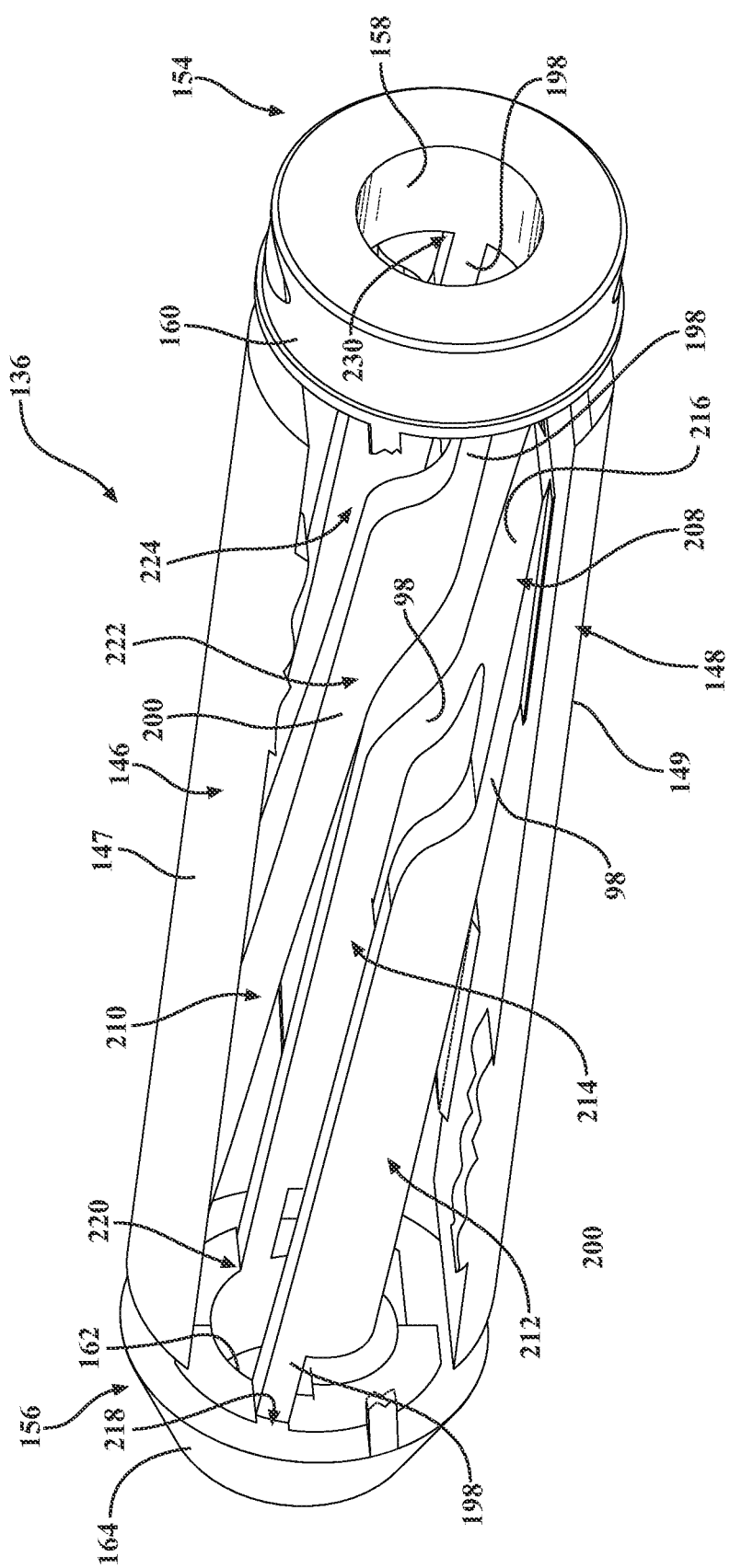
FIG. 14 is a sectional view of the implant of FIG. 13 taken along lines 5-5.

Referring now to FIGS. 13-17, the implant 136 includes a lower support fork 208 and an upper support fork 210. In a broadest sense, with the first, second, third, and fourth supports 166, 168, 170, 172 being arranged in parallel as previously described, the lower and upper support forks 208, 210 provide the crisscross configuration in the proximal-to-distal direction, and thus facilitate the greater expansion-to-length ratio of the implant 136. As best shown in FIGS. 14 and 17, the lower support fork 208 includes a pair of supports 212, 214. The supports 212, 214 may be arranged in a V-shaped configuration to converge at an apex 216. The apex 216 may be considered a proximal end of the lower support fork 208 with the apex 216 coupled to the upper side 181 of the lower plate 148. In certain implementations, the supports 212, 214 may be discrete structures parallel to or angled relative to one another with each of the supports 212, 214 having respective proximal ends coupled to the lower plate 148. One of the supports of the lower support fork 208 (hereinafter referred to as a fifth support 212) may extend from the apex 212 to a distal end 218 coupled to the distal end portion 156, as shown in FIG. 14. The other support (hereinafter referred to as a sixth support 214) may extend from the apex 212 to a distal end 220 coupled to the distal end portion 156.

The upper support fork 210 includes a pair of supports 222, 224. The supports 222, 224 may be arranged in a V-shaped configuration to converge at an apex 226 (see FIGS. 15 and 19). The apex 226 may be considered a distal end of the upper support fork 210 with the apex 226 coupled to the underside 180 of the upper plate 146. In certain implementations, the supports 222, 224 may be discrete structures parallel to or angled relative to one another with each of the supports 222, 224 having respective proximal ends coupled to the upper plate 146. One of the supports of the upper support fork 210 (hereinafter referred to as a seventh support 222) may extend from the apex 216 to a proximal end 228 coupled to the proximal end portion 154, as best shown in FIG. 17. The other support (hereinafter referred to as an eight support 224) may extend from the apex 216 to a proximal end 230 coupled to the proximal end portion 154. The lower and upper support forks 208, 210 may be arranged at least substantially parallel to one another in the insertion configuration, as best shown in FIG. 14, and in the deployed configuration.

The lower support fork 208 and/or the upper support forks 210 are arranged in the crisscross configuration with at least one of the first, second, third, and fourth supports 166, 168, 170, 172. Referring now to FIG. 15, the proximal ends 176, 182 of the first and second supports 166, 168, respectively, are coupled to the upper plate 146 at an axial position closer to the proximal end portion 154 than an axial position where the distal end (e.g., the apex 226) of the upper support fork 210 is coupled to the upper plate 146. In other words, the axial position where the first and second supports 166, 168 is coupled to the upper plate 146 is defined as axes $A_1, A_2$, and the axial position where the upper support fork 210 is coupled to the upper plate 146 is identified as axis $A_{UF}$. The axis $A_{UF}$ is distal to the axes $A_1, A_2$. Stated more simply, the first and second supports 166, 168 are arranged in the crisscross configuration in the proximal-to-distal direction with the upper support fork 210 when viewed in elevation. Likewise, the distal ends 188, 196 of the third and fourth supports 170, 172, respectively, are coupled to the lower plate 148 at an axial position closer to the distal end portion 156 than an axial position where the proximal end (e.g., the apex 216) of the lower support fork 208 is coupled to the lower plate 148. In other words, the axial position where the third and fourth supports 170, 178 are coupled to the lower plate 148 is defined as axes $A_3, A_3$, and the axial position where the lower support fork 208 is coupled to the lower plate 148 is identified as axis $A_{LF}$. The axis $A_{LF}$ is proximal to the axes $A_3, A_3$. Again, stated more simply, the third and fourth supports 170, 172 are arranged in the crisscross configuration in the proximal-to-distal direction with the lower support fork 208 when viewed in elevation. The collectively arrangement of the first through eighth supports 166-172, 212, 214, 222, 224 may be considered conceptually somewhat similar to the tines of two flatware forks being intersected with one another.

The fifth, sixth, seventh, and/or eighth supports 212, 214, 222, 224 may include the material webs 198 having reduced thickness portions configured to plastically deform as said implant 136 is deployed within the vertebral body 26. The fifth, sixth, seventh, and/or eighth supports 212, 214, 222, 224 may include the strut portion 200 and the material webs 198 positioned on one side or opposing sides of the strut portion 200. A thickness of the strut portion 200 is greater than the thickness of the material webs 198 such that, as the implant 136 is moved from the insertion configuration to the deployed configuration, stresses are localized to impart bending of the material webs 198.

Referring now to FIG. 17 showing a top plan view of the implant 136 in section, the first support 166 and the fourth support 172 are spaced apart laterally from the second support 168 and the third support 170. In other words, the first and third supports 166, 170 may be considered an opposing lateral pair of supports, and the second and fourth supports 168, 172 may be considered another opposing lateral pair of supports. Moreover, the fifth support 212 and the sixth support 214 of the lower support fork 208 are spaced apart laterally from one another, and the seventh support 222 and the eight support 224 are spaced apart laterally from one another. The aforementioned lateral spacing defines the void space 102. The void space 102 is in communication with the bores 158, 162 defined by the proximal and distal end portions 154, 156, and the retaining element 144 is at least partially disposed in the void space 202.

Figure 18:
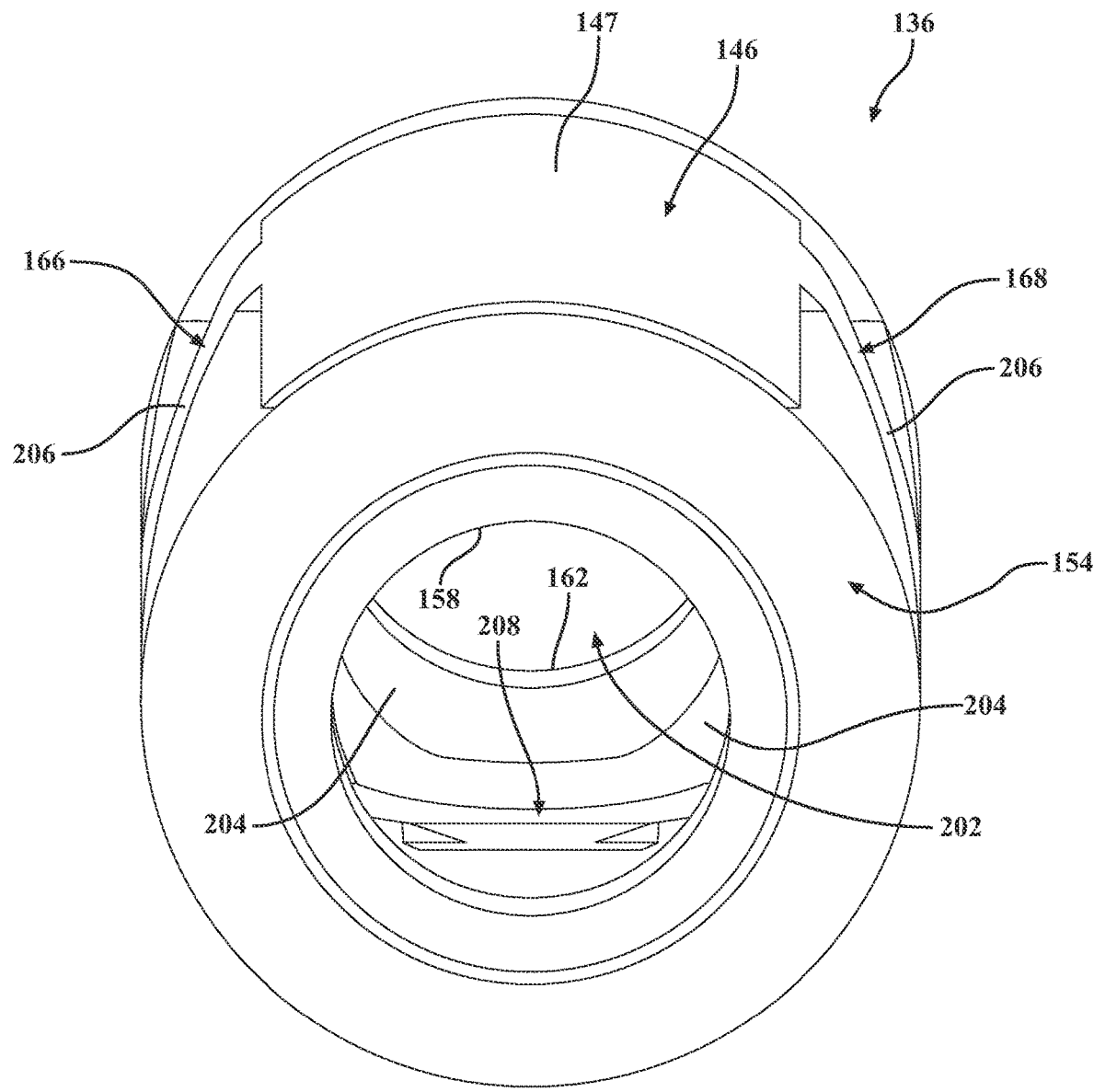
FIG. 18 is an axial upper perspective view of the implant of FIG. 13.
Figure 19:
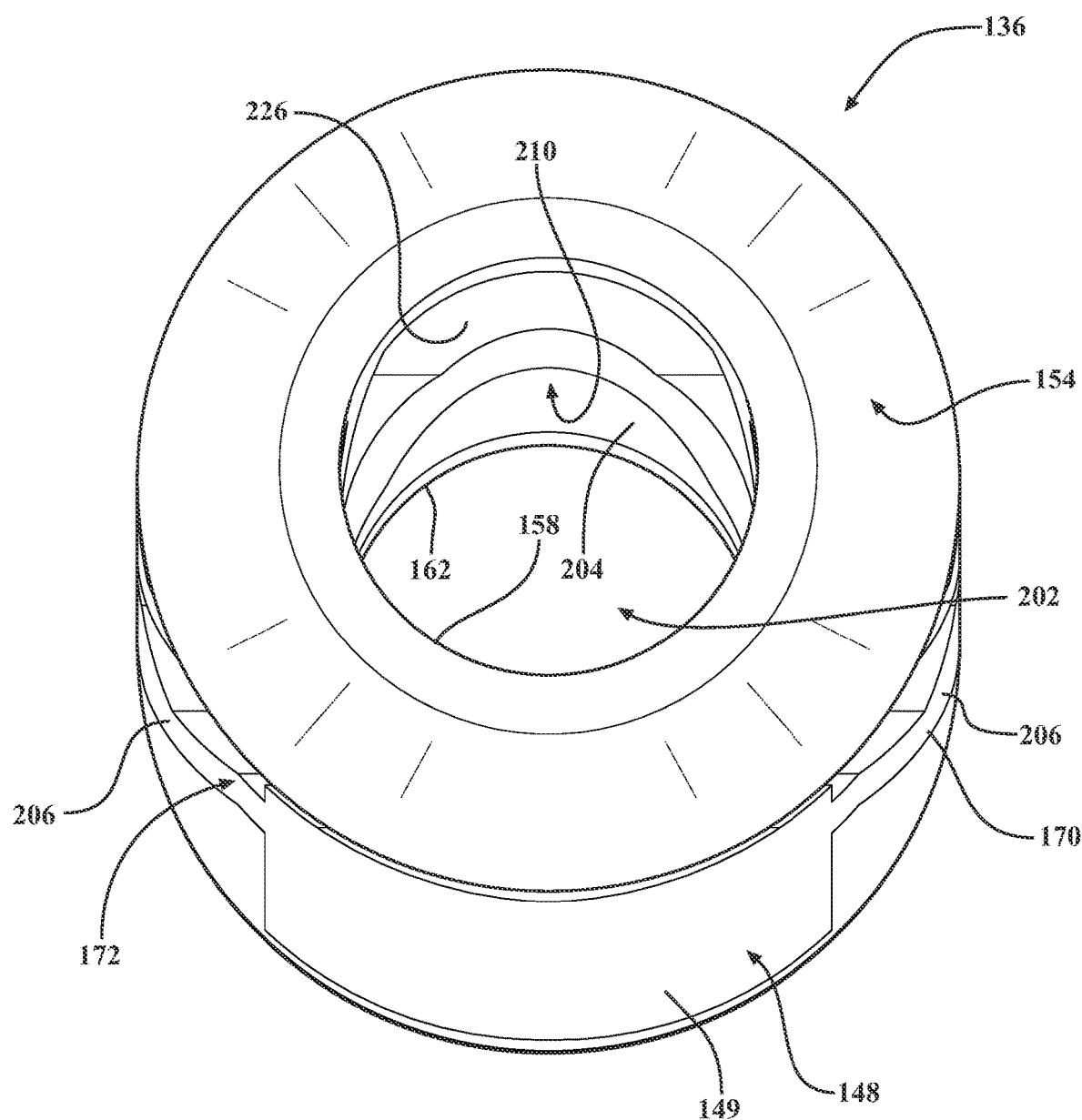
FIG. 19 is an axial lower perspective view of the implant of FIG. 13.

As previously explained, the retaining element 44 may be a cylindrical stem. In such an implantation, the fifth, sixth, seventh, and eighth supports 212, 214, 222, 224 may collectively define a generally cylindrical shaped channel extending through the implant 136 in the proximal-to-distal direction, as shown in FIGS. 18 and 19. Each of the fifth, sixth, seventh, and eighth supports 212, 214, 222, 224 may include the arcuate inner surface 204. The apexes 216, 226 may also include the arcuate inner surface 204. Further, the first, second, third, fourth supports 166, 168, 170, 172 may also collectively define a generally cylindrical shaped channel within which the lower and upper support forks 208, 210 are disposed. Each of the first, second, third, and fourth supports 66, 68, 70, 72 may include another arcuate inner surface generally contoured to arcuate outer surfaces of the fifth, sixth, seventh, and eighth supports 212, 214, 222, 224. The arcuate inner surface 204 may be on the material webs 198 and/or the strut portions 200. And the cylindrical profile may complementary to the bores 158, 162 of the proximal and distal end portions 154, 156. Each of the first, second, third, and fourth supports 166, 168, 170, 172 may further include the arcuate outer surface 206 opposite the arcuate inner surface. The loadbearing surfaces 147, 149 of the upper and lower plates 146, 148 may be arcuate in shape to collectively provide the implant 136 with a generally cylindrical outer profile. The generally cylindrical outer profile of less than six millimeters so as to be deployable through the lumen of the introducer device 34. As previously explained, the complex, overlapping structures of the implant 36, 136 may render certain conventional manufacturing techniques unsuitable, challenges which may be even more pronounced with the implant 136 including the lower and upper support forks 208, 210. The use of additive manufacturing techniques may be particularly well suited for overcome such manufacturing challenges.

Figure 22:
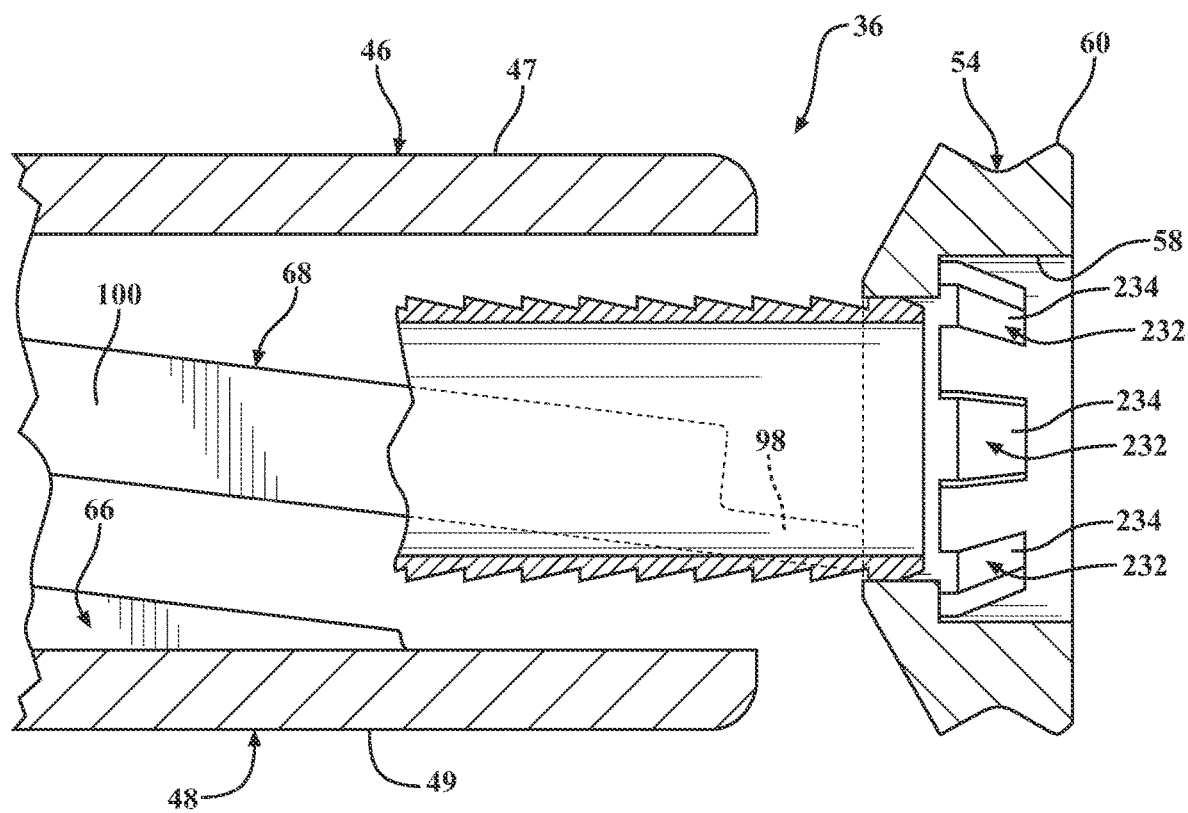
FIG. 22 is a sectional elevation view of a portion of the implant of FIG. 2 with a proximal end portion including castellations.

With the advantageous increased expansion capabilities realized by the implant 36, 136 of the present disclosure, it may be desirable to improved locking of the retaining element 44 during and after deployment. In other words, as the implant 36, 136 is displacing elevating or restoring the vertebral body 26 to increasing heights, the forces on the loadbearing surfaces 47, 147, 49, 149 of the upper and lower plates 46, 146, 48, 148, respectively, may be correspondingly increased. Referring now to FIG. 22, a portion of the implant 36 is shown with the retaining element 44 and a modified proximal end portion 54. The retaining element 44 may include the locking features 52 previously introduced. The locking features 52 may be similar to one-way teeth with steeper-sloped surfaces on the distal side of the teeth to provide interference engagement and prevent distal movement of the retaining element 44 relative to the proximal end portion 54 once the complementary locking feature has moved past a particular tooth. The proximal end portion 54 may include castellations 232 arranged annularly with each of the castellations 232 including an inwardly sloping protrusion 234. The diameter between protrusions 234 of diametrically opposed pairs of the castellations 232 may be slightly less than an outer diameter of the locking features 52 of the retaining element 44. As such, as the locking features 52 move proximally past the castellations 232—for example, via a threaded interface or via linear movement—distal ends of the protrusions 234 provide the aforementioned interference engagement. The interference engagement may be especially robust to advantageously maintain the implant 36, 136 in the deployed configuration that has been selectively tuned by the practitioner, particularly as the vertebral body 26 is restored to increased heights capable with the implant 36, 136 of the present disclosure.

In certain implementations, the geometries of the castellations 232 including the protrusions 234 may be particularly well suited to be fabricated through additive manufacturing. Doing so—together with the materials typically utilized in additive manufacturing—may provide for the castellations 232 being deflectable and resilient. As a result, as the locking features 52 of the retaining element 44 move past the castellations 232, the castellations 232 may resiliently deflect to better engage the locking features 52. Other machining process may result in plastic deformation or damage as the locking feature 52 move past the complementary locking feature(s), and thus reduce retention of the retaining element 44. It is further contemplated that the retaining element 44 may also be fabricated through additive manufacturing, for example, in a single process together with the implant 36, 136.

Certain implementations may be described with reference to the following exemplary clauses:

Clause 1—An implant for restoring height of a vertebral body, the implant configured to be deployed in the craniocaudal direction within the vertebral body after being directed through an access cannula with an introducer device, the implant including: an upper plate and a lower plate arranged parallel to one another and respectively forming upper and lower loadbearing surfaces for the vertebral body; a distal end portion and a proximal end portion positioned opposite the upper and lower plates; a first support disposed between the upper and lower plates, the first support including a distal end coupled to the distal end portion and a proximal end coupled to the upper plate; and a second support disposed between the upper and lower plates, the second support including a proximal end coupled to the proximal end portion and a distal end coupled to the upper plate, wherein the proximal end of the first support is coupled to the upper plate at an axial position closer to the proximal end portion than an axial position where the distal end of the second support is coupled to the upper plate.

The implant of clause 1, wherein the first and second supports each comprise material webs including reduced thickness portions configured to plastically deform as the implant is deployed within the vertebral body.

The implant of clause 1, further including: a third support disposed between the upper and lower plates, the third support including a distal end coupled to the distal end portion and a proximal end coupled to the lower plate; and a fourth support disposed between the upper and lower plates, the fourth support including a distal end coupled to the lower plate and a proximal end coupled to the proximal end portion, wherein the proximal end of the third support is coupled to the lower plate at an axial position closer to the proximal end portion than an axial position of where the distal end of the fourth support is coupled to the lower plate.

The implant of clause 3, wherein the third and fourth supports each comprise material webs including reduced thickness portions configured to plastically deform as the implant is deployed within the vertebral body.

The implant of clauses 3 or 4, wherein the proximal end of the first support is coupled to the upper plate at an axial position closer to the proximal end portion than an axial position of where the distal end of the fourth support is coupled to the lower plate.

The implant of clause 5, wherein the distal end of the second support is coupled to the upper plate at an axial position closer to the distal end portion than an axial position of where the proximal end of the third support is coupled to the lower plate.

The implant of clause 6, wherein the distal end portion and the proximal end portion each define a bore coaxial with a longitudinal axis of the implant.

The implant of any one of clauses 7, wherein the first and fourth supports are spaced apart laterally from the second and third supports to define a void space in communication with the coaxial bores.

The implant of clause 8, further including a retaining element at least partially disposed within the void space, the retaining element configured to deploy the implant and to retain the implant after deployment.

The implant of any one of clauses 1-9, further including an upper support fork including a pair of supports arranged in a V-shaped configuration, the upper support fork positioned between the upper and lower plates and coupled to the upper plate and the proximal end portion.

The implant of clause 10, further including a lower support fork including a pair of supports arranged in a V-shaped configuration, the lower support fork positioned between the upper and lower plates and coupled to the lower plate and the distal end portion.

An implant for restoring height of a vertebral body, the implant configured to be deployed in the craniocaudal direction within the vertebral body after being directed through an access cannula with an introducer device, the implant including: an upper plate and a lower plate respectively forming first and second loadbearing surfaces for the vertebral body, the implant configured to be directed through the access cannula in an insertion configuration in which the upper and lower plates are spaced apart at a first distance, and expanded to a deployed configuration in which the upper and lower plates are moved away from one another in the craniocaudal direction to a second distance greater than the first distance, wherein each of the upper and lower plates are substantially parallel to a longitudinal axis of the implant that extends in a proximal-to-distal direction; and a first pair of supports coupled to the upper plate and disposed between the upper and lower plates, the first pair of supports arranged in a crisscross configuration in the proximal-to-distal direction in each of the insertion configuration and the deployed configuration.

The implant of clause 12, wherein each of the first pair of supports includes material webs including reduced thickness portions configured to plastically deform as the implant moves from the insertion configuration to the deployed configuration.

The implant of clauses 12 or 13, further including a second pair of supports coupled to the lower plate and disposed between the upper and lower plates, the first pair of supports arranged in a crisscross configuration in the proximal-to-distal direction in each of the insertion configuration and the deployed configuration.

The implant of clause 14, wherein each of the second pair of supports includes material webs including reduced thickness portions configured to plastically deform as the implant moves from the insertion configuration to the deployed configuration.

The implant of clauses 14 or 15, further including a distal end portion coupled to one of the first pair of supports and coupled to one of the second pair of supports, the distal end portion defining a first bore coaxial with the longitudinal axis of the implant.

The implant of clause 16, further including a proximal end portion coupled to the other one of the first pair of supports and coupled to the other one of the second pair of supports, the proximal end portion defining a second bore coaxial with the first bore and coaxial with the longitudinal axis of the implant.

The implant of any one of clauses 12-17, wherein the first pair of supports are positioned opposite the longitudinal axis and spaced apart from one another to define a void space.

The implant of clause 18, further including a retaining element at least partially disposed within the void space, the retaining element configured to move the implant from the insertion configuration to the deployed configuration, and retain the implant in a deployed configuration.

The implant of clause 14, wherein each of the first pair of supports are substantially parallel to one of the second pair of supports in the insertion configuration and the deployed configuration.

The implant of any one of clauses 12-20, further including an upper support fork including a third pair of supports arranged in a V-shaped configuration, the upper support fork positioned between the upper and lower plates and coupled to the upper plate and the proximal end portion.

The implant of clause 21, further including a lower support fork including a pair of supports arranged in a V-shaped configuration, the lower support fork positioned between the upper and lower plates and coupled to the lower plate and the distal end portion.

An implant for restoring height of a vertebral body, the implant configured to be deployed in the craniocaudal direction within the vertebral body after being directed through an access cannula with an introducer device, the implant including: an upper plate and a lower plate respectively forming upper and lower loadbearing surfaces for the vertebral body, the implant configured to be directed through the access cannula in an insertion configuration in which the upper and lower plates are spaced apart at a first distance, and expanded to a deployed configuration in which the upper and lower plates are moved away from one another in the craniocaudal direction to be spaced apart at a second distance greater than the first distance, wherein each of the upper and lower plates are substantially parallel to a longitudinal axis of the implant in the insertion and deployed configurations; and a distal end portion and a proximal end portion positioned opposite the upper and lower plates; a first support coupled to the distal end portion and the upper plate; a second support coupled to the proximal end portion and the upper plate; a third support coupled to the distal end portion and the lower plate; and a fourth support coupled to the proximal end portion and the lower plate; wherein the first and fourth supports are arranged substantially parallel to one another in each of the insertion configuration and the deployed configuration, wherein the second and third supports are arranged substantially parallel to one another in each of the insertion configuration and the deployed configuration.

The implant of clause 23, wherein each of the first, second, third and fourth supports includes material webs including reduced thickness portions configured to plastically deform as the implant moves from the insertion configuration to the deployed configuration.

The implant of clauses 29 or 30, wherein the first and second supports are spaced apart from one another on opposing sides the implant.

The implant of clause 31, wherein the third and fourth supports are spaced apart from one another on opposing sides the implant.

The implant of clauses 29-32, wherein each of the first, second, third and fourth supports includes an arcuate inner surface with the arcuate inner surfaces collectively defining a void space having a generally cylindrical profile.

The implant of clause 33, wherein each of the first, second, third and fourth supports includes an arcuate outer surface opposite the arcuate inner surface with the arcuate outer surfaces complementing the upper and lower plates to provide the implant with a generally cylindrical profile.

An implant for restoring height of a vertebral body, the implant configured to be deployed in the craniocaudal direction within the vertebral body after being directed through an access cannula with an introducer device, the implant including: an upper plate and a lower plate respectively forming first and second loadbearing surfaces for the vertebral body, the implant configured to be directed through the access cannula in an insertion configuration in which the upper and lower plates are spaced apart at a first distance, and expanded to a deployed configuration in which the upper and lower plates are moved away from one another in the craniocaudal direction to a second distance greater than the first distance, wherein each of the upper and lower plates are substantially parallel to a longitudinal axis of the implant that extends in a proximal-to-distal direction; a distal end portion and a proximal end portion positioned opposite the upper and lower plates in the insertion configuration; and a pair of supports coupled to the upper plate and disposed between the upper and lower plates, the first pair of supports arranged to intersect, in each of the insertion configuration and the deployed configuration, a plane perpendicular to the longitudinal axis that bifurcates the implant between the distal end and proximal end portions.

The foregoing disclosure is not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:

1. An implant for restoring height of a vertebral body, the implant configured to be deployed in a craniocaudal direction within the vertebral body after being directed through an access cannula with an introducer device, the implant comprising:
   an upper plate and a lower plate configured to respectively form upper and lower loadbearing surfaces;
   a distal end portion and a proximal end portion;
   a first support coupled to the distal end portion and an underside of the upper plate;
   a second support coupled to the proximal end portion and the underside of the upper plate, wherein the first support and the second support are arranged to crisscross in a proximal-to-distal direction;
   a third support coupled to the distal end portion and an upper side of the lower plate; and
   a fourth support coupled to the proximal end portion and the upper side of the lower plate, wherein the third support and the fourth support are arranged to crisscross in the proximal-to-distal direction,
   wherein the first support is coupled to the upper plate at an axial position that is proximal to where the second support is coupled to the upper plate,
   wherein the third support is coupled to the lower plate at an axial position that is proximal to where the fourth support is coupled to the lower plate.

2. The implant of claim 1, wherein the implant is configured to be moved from an insertion configuration to a deployed configuration in which the first, second, third and fourth supports articulate to move the upper plate and the lower plate away from one another, wherein the first and second supports are arranged to remain crisscross in the deployed configuration, and wherein the third and fourth supports are arranged to remain crisscross in the deployed configuration.

3. The implant of claim 1, wherein the first support is not directly connected to the lower plate and the proximal end portion.

4. The implant of claim 3, wherein the second support is not directly connected to the lower plate and the distal end portion.

5. The implant of claim 4, wherein the first support is on a first lateral side of the implant, and the second support is one a second lateral side of the implant.

6. The implant of claim 1, further comprising an upper support fork positioned between the upper and lower plates and comprising a proximal end coupled to the upper plate, and a pair of supports coupled to the proximal end portion.

7. The implant of claim 6, wherein the pair of supports of the upper support fork are arranged in a V-shaped configuration to converge at an apex that is coupled to the underside of the upper plate.

8. The implant of claim 1, wherein fixed lengths of the first and second supports being within the range of approximately 60-75% of the fixed length of the upper and lower plates.

9. The implant of claim 1, wherein the upper plate, the lower plate, the proximal end portion, the distal end portion, the first support, and the second support are formed through additive manufacturing.

10. An implant for restoring height of a vertebral body, the implant configured to be deployed in a craniocaudal direction within the vertebral body after being directed through an access cannula with an introducer device, the implant comprising:
    an upper plate and a lower plate configured to respectively form upper and lower loadbearing surfaces;
    a distal end portion and a proximal end portion that define coaxial bores;
    a first support coupled to the distal end portion and an underside of the upper plate;
    a second support coupled to the distal end portion and the underside of the upper plate, wherein the first support and the second support are disposed on opposing lateral sides of the implant to define a void space therebetween;
    a lower support fork comprising a pair of supports disposed in the void space with each of the pair of supports comprising an arcuate inner surface; and
    a retaining element being cylindrical in shape and extending through the coaxial bores of the distal end portion and the proximal end portion and a cylindrical profile defined by the arcuate inner surfaces of the pair of supports of the lower support fork.

11. The implant of claim 10, wherein the pair of supports of the lower support fork diverge from an apex to the opposing lateral sides of the implant.

12. The implant of claim 10, further comprising an upper support fork comprising a pair of supports disposed in the void space with each of the pair of supports comprising an arcuate inner surface.

13. The implant of claim 12, wherein the pair of supports of the upper support fork diverge from an apex to the opposing lateral sides of the implant.

14. The implant of claim 10, where each of the pair of supports further comprise an arcuate outer surface opposite the arcuate inner surface.

15. An implant for restoring height of a vertebral body, the implant configured to be deployed in a craniocaudal direction within the vertebral body after being directed through an access cannula with an introducer device, the implant comprising:
    an upper plate and a lower plate configured to respectively form upper and lower loadbearing surfaces;
    a distal end portion and a proximal end portion;
    a first support coupled to the distal end portion and an underside of the upper plate;
    a second support coupled to the proximal end portion and the underside of the upper plate, wherein the first support and the second support are arranged to crisscross in a proximal-to-distal direction;

a third support coupled to the distal end portion and an upper side of the lower plate; and a fourth support coupled to the proximal end portion and the upper side of the lower plate, wherein the third support and the fourth support are arranged to criss-cross in the proximal-to-distal direction, wherein fixed lengths of the first and second supports being within the range of approximately 60-75% of the fixed length of the upper and lower plates.

16. The implant of claim 1, wherein the implant is configured to be moved from an insertion configuration to a deployed configuration in which the first, second, third and fourth supports articulate to move the upper plate and the lower plate away from one another, wherein the first and second supports are arranged to remain crisscross in the deployed configuration, and wherein the third and fourth supports are arranged to remain crisscross in the deployed configuration.

17. The implant of claim 15, wherein the first support is not directly connected to the lower plate and the proximal end portion, and wherein the second support is not directly connected to the lower plate and the distal end portion.

18. The implant of claim 15, further comprising an upper support fork positioned between the upper and lower plates and comprising a proximal end coupled to the upper plate, and a pair of supports coupled to the proximal end portion.

19. The implant of claim 15, wherein the first support is on a first lateral side of the implant, and the second support is one a second lateral side of the implant.

* * * * *